United States Patent
Nozoe et al.

[11] Patent Number: 5,840,927
[45] Date of Patent: Nov. 24, 1998

[54] SESQUITERPENE COMPOUNDS

[75] Inventors: Shigeo Nozoe, Sendai; Akira Takahashi, Tsukuba; Jun-ich Masuda, Tsukuba; Ken-ichi Tanaka, Tsukuba; Hideo Suzuki, Tsukuba, all of Japan

[73] Assignee: Toa Gosei Co., Ltd., Japan

[21] Appl. No.: 894,312

[22] PCT Filed: Feb. 14, 1996

[86] PCT No.: PCT/JP96/00315

§ 371 Date: Sep. 26, 1997

§ 102(e) Date: Sep. 26, 1997

[87] PCT Pub. No.: WO96/25385

PCT Pub. Date: Aug. 22, 1996

[30] Foreign Application Priority Data

Feb. 15, 1995 [JP] Japan ................ 7-050474

[51] Int. Cl.⁶ ............ C07D 307/92; C07D 307/91
[52] U.S. Cl. ............ 549/458; 549/460; 549/461
[58] Field of Search ............ 549/458, 460, 549/461

[56] References Cited

FOREIGN PATENT DOCUMENTS 55-136285 10/1980 Japan .
7-61980 3/1995 Japan .

OTHER PUBLICATIONS

Asakawa et al., *Trans. mycol. Soc. Japan*, 29:281–296 (1988).
Hashimoto et al., "The bitter sesquiterpenoids from the fungus *Cryptoporus volvatus*", *Trans. Mycol. Soc. Japan*, 29:281–296 (1988).
Hirotani et al., *Phytochemistry*, 30(5):1555–1559 (1991).
Lee et al., "Studies on the Constituents of Higher Fungi of Korea", *Kor. J. Mycol.*, 9(3):153–155 (1981).
Kim et al., "Antitumor Components of *Cryptoporus volvatus*", *Kor. j. Mycol.*, 10(3):111–117 (1982).

*Primary Examiner*—Johann Richter
*Assistant Examiner*—Dominic Keating
*Attorney, Agent, or Firm*—Fish & Richardson P.C.

[57] ABSTRACT

Novel anti-microbial sesquiterpene compounds isolated from the fruit bodies of *Roseofomes subflexibilis* (Hounentake) having the general formula 6 Claims, 31 Drawing Sheets

SESQUITERPENE COMPOUNDS

FIELD OF THE INVENTION

The present invention relates to a new family of sesquiterpene compounds which are isolated from fruit bodies of Basidiomycota, and expected to be applied to the medication because of their anti-fungal activities.

BACKGROUND OF THE INVENTION

Development of anti-microbial drugs with antibiotics playing the central role has been achieved remarkably, while that of anti-fungal drugs is not necessarily satisfactory from the perspective of their varieties and effectivities. Especially, the opportunistic mycoses of internal organs caused by infections with Candida, Aspergillus and Cryptococcus mycetes due to the decrease in bodily defense capability induced by extensive administration of carcinostatic agents, immunosuppressants, steroid hormones, etc. as well as AIDS (acquired immunodeficiency syndrome) in recent years are posing an important medical problem. Therefore, there is a strong demand for the development of remedies for mycoses.

On the other hand, physiologically active ingredients contained in mushrooms have been examined extensively since olden times. *Elfvingia applanata* (kofuki-saru-no-koshikake, Ganodermataceae) and *Coriolus versicolor* (Kawara-take, Polyporaceae have been used as legendary herb medicines or folk medicines for gastric cancer, esophagus cancer, breast cancer, prostate cancer, etc. Especially, β-D-glucan-protein complex (PS-K) extracted from mycelia of Coriolaceae (Kawara-take) in culture has been used extensively as a carcinostatic agent. Furthermore, the isolation of a carcinostatic protein-polysaccharide from aqueous extracts and ergosterol from $CHCl_3$-MeOH extracts of Hitokuchitake, has been reported by Lee et al. (1981) and Kim et al. (1982) in Korea, respectively [Asakawa et al., Trans. Mycol. Soc. Japan, 29, 281–296 (1988)]. Furthermore, the isolation of cryptoporic acids A–G [Asakawa et al., Trans. Mycol. Soc. Japan, 29, 281–296 (1988); Asakawa et al., Phytochemistry, 31(2), 579–592 (1992)], and cryptoporic acid H [M. Hirotani et al., Phytochemistry, 30 (5), 1555–1559 ( 1991)] from this Hitokuchitake has been reported.

SUMMARY OF THE INVENTION

Searching for novel physiologically active ingredients contained mushrooms, the present inventors made tremendous efforts to find compounds having strong anti-fungal activity against the above mentioned eumycetes which induce the opportunistic mycosis of internal organs, that is, compounds effectively usable as anti-fungal agents. The present invention aims at providing effective compounds as anti-fungal agents.

Based on thorough study, the present inventors succeeded in isolating novel sesquiterpene compounds from the lower alcohol or acetone extracts of fruit bodies of *Roseofomes subflexibilis* (Hounen-take) (Berk. et Curt. Aoshi.) in Polyporaceae family, and accomplished the present invention by further finding the anti-fungal activity of these compounds in the assay of antibiotic action. In the chemical formulas described in the present invention, when residues denoted by $R^1$ are present plurally in a given compound, they may represent the same residue or different ones. The same rule will be applied to $R^3$ and $R^4$.

Namely, the present invention relates to sesquiterpene compounds represented by the following general structural formula I:

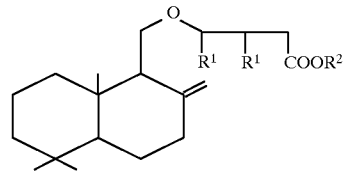

(I)

wherein one of the two $R^1$ groups is —$COOR^3$, and the other one is any one of the groups represented by the following formulas, wherein $R^2$ and $R^3$ are hydrogen atom or alkyl group, and $R^4$ is hydroxyl group or alkoxy group.

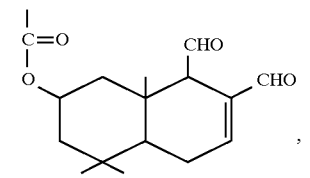

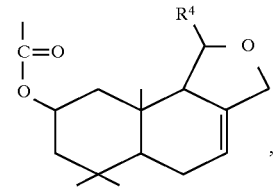

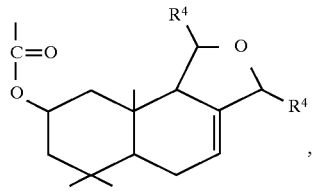

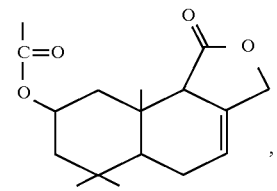

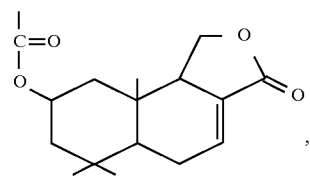

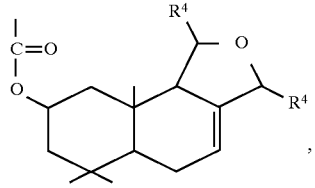

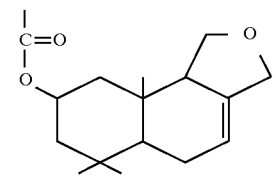

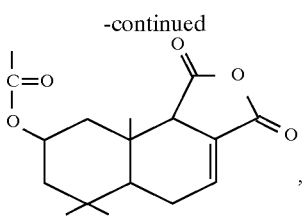

In the most preferred embodiments of the present invention, $R^2$ and $R^3$ are hydrogen atom or lower alkyl group, and $R^4$ is hydroxyl group.

The present invention also includes anti-microbial agents comprising sesquiterpene compounds represented by the following general formula II:

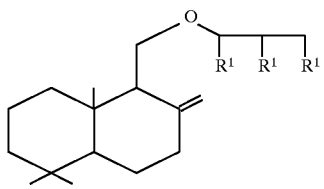
(II)

wherein $R^1$ is —COOR$^2$ group (wherein $R^2$ is hydrogen atom, alkyl group or acyloxyalkyl group), or any one of the groups represented by the following formulas (wherein $R^3$ is hydroxyl group or alkoxy group).

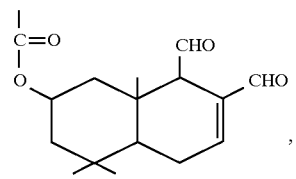

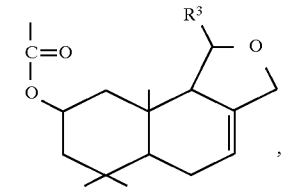

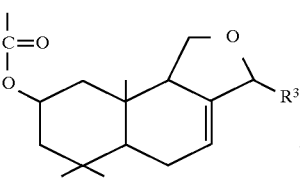

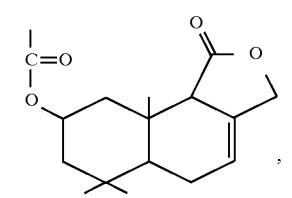

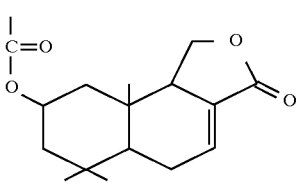

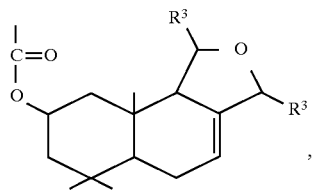

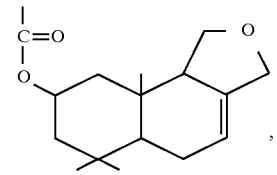

Of these anti-microbial agents described above, those comprising sesquiterpene compounds represented by the following Formula I are most preferable:

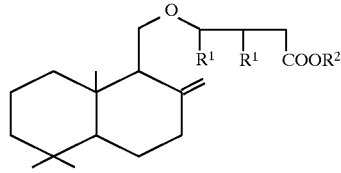
(I)

wherein one of the two $R^1$s in Formula I is —COOR$^3$ group, and the other one is COOH group or any one of the groups represented by the following formulas, wherein $R^2$ and $R^3$ are independently hydrogen atom, alkyl group or acyloxyalkyl group, or are both hydrogen atoms when the other one of $R^1$ group described above is —COOH, and $R^4$ is hydroxyl group or alkoxy group.

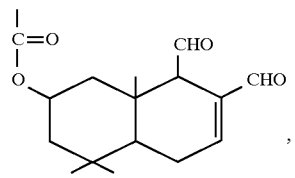

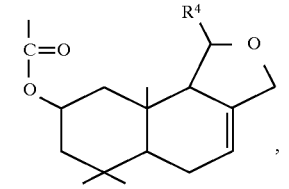

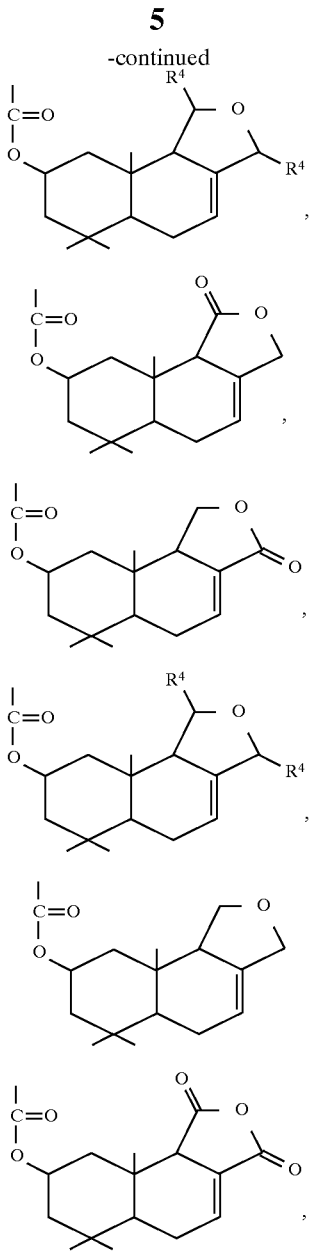

DETAILED DESCRIPTION OF THE INVENTION

Firstly, the method for isolating the novel compounds of the present invention from *Roseofomes subflexibilis* (Hounen-take) in Polyporaceae family will be described.

The novel compounds of this invention can be extracted from fruit bodies of *Roseofomes subflexibilis* (Hounen-take) in Polyporaceae family which is mainly grown on fallen timbers in coppice from summer to autumn.

Fruit bodies of Hounen-take are finely minced, and immersed in acetone or lower alcohol such as methanol at room temperature for 1 to 3 days. After the extract is concentrated in vacuo, the syrupy residue is suspended in water, and extracted with ethyl acetate. The ethyl acetate extract thus obtained is purified by silica gel chromatography and preparative thin layer chromatography conventionally used for separating antibiotics, and further in combination with high performance liquid chromatography to fractionate the novel compounds of the present invention including TG101, TG102, TG103, TG104, and other cryptoporic acid A (CA-A).

Although these novel compounds can not be crystallized, they can be obtained as colorless or pale yellow powder by selecting the suitable solvent to dissolve them, and drying the compounds by evaporating the solvent. Furthermore, derivatives of each isolated compound can be produced by chemical syntheses.

In the following, the method for preparing novel compounds of the present invention will be described with reference to examples, but they should not be construed to limit this invention.

MOST PREFERRED EMBODIMENTS FOR CARRYING OUT THE INVENTION

Example 1

Figure 1:
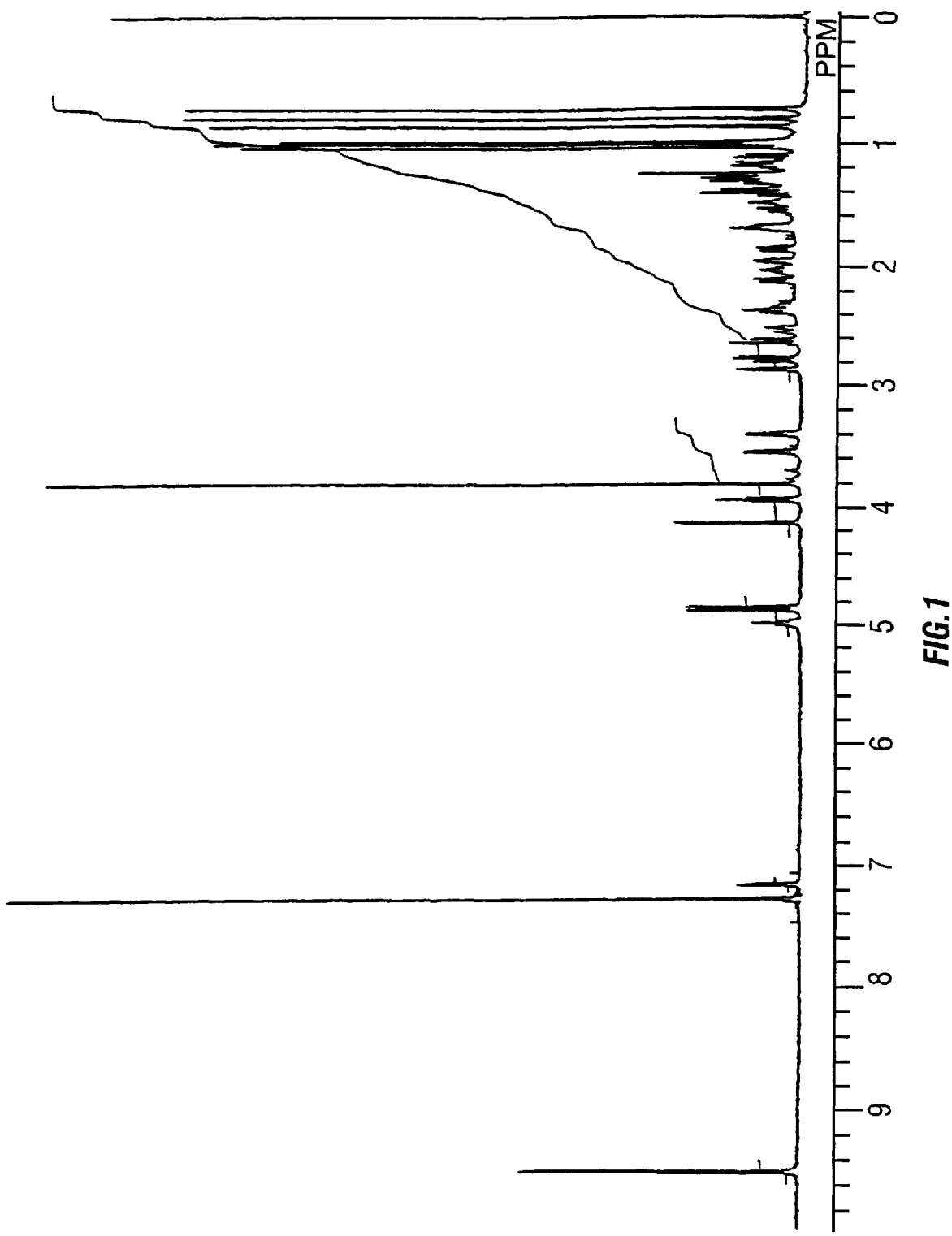
FIG. 1 shows $^1$H NMR (500 MHz; CDCl$_3$) spectrum of TG101.

Isolation of TG101, TG102, TG103, and TG104 from *Roseofomes subflexibilis* (Hounen-take)

Fruit bodies (60 g) of Hounen-take harvested at Aoba-yama in Sendai City, Japan, in October, 1992 were immersed in acetone (300 ml) for one day to obtain the acetone-extract, and then the insoluble residue was further immersed in methanol (30 ml) to obtain the methanol-extract. After each solvent of the two extracts was distilled off in vacuo, water (25 ml) was added to each residue, and extracted with ethyl acetate (50 ml, twice). After both of the ethyl acetate soluble fractions thus obtained were confirmed to contain novel compounds by thin layer chromatography, these fractions were combined.

The combined ethyl acetate soluble fraction (1.52 g) was subjected to silica gel column chromatography (16 g; 1.5 cm internal diameter×20 cm), and eluted successively with the mixed eluents: n-hexane/ethyl acetate, chloroform/ethyl acetate, and chloroform/methanol.

After fractions eluted with chloroform/methanol (95/5 to 90/10) were combined and concentrated in vacuo, the residue thus obtained (308 mg) was further fractionated by silica gel column chromatography (eluent, chloroform/methanol= 99/1 to 90/10) to obtain the fraction (149 mg) was eluted with chloroform/methanol (98/2 to 96/4).

On the other hand, the fraction (161 mg) eluted with chloroform/methanol (90/10 to 80/20) was similarly fractionated to obtain the fraction (68 mg) eluted with chloroform/methanol (95/5 to 90/10).

These fractions thus obtained were purified by preparative thin layer chromatography [on TLC plate of silica gel 60 F$_{254}$, 20 cm×20 cm×0.5 mm (E. Merck); eluent, chloroform/methanol=95/5 to 90/10 ) to yield four kinds of colorless or pale yellow syrupy novel compounds.

Yields of the compounds designated TG101, TG102, TG103 and TG104 were 52.3 mg, 2.8 mg, 31.1 mg and 5.4 mg, respectively.

The structural formulas and physico-chemical properties of novel compounds isolated from Hounen-take described above are as follows:

Structural Formula of TG101

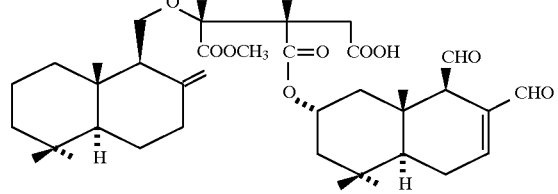

Figure 2:
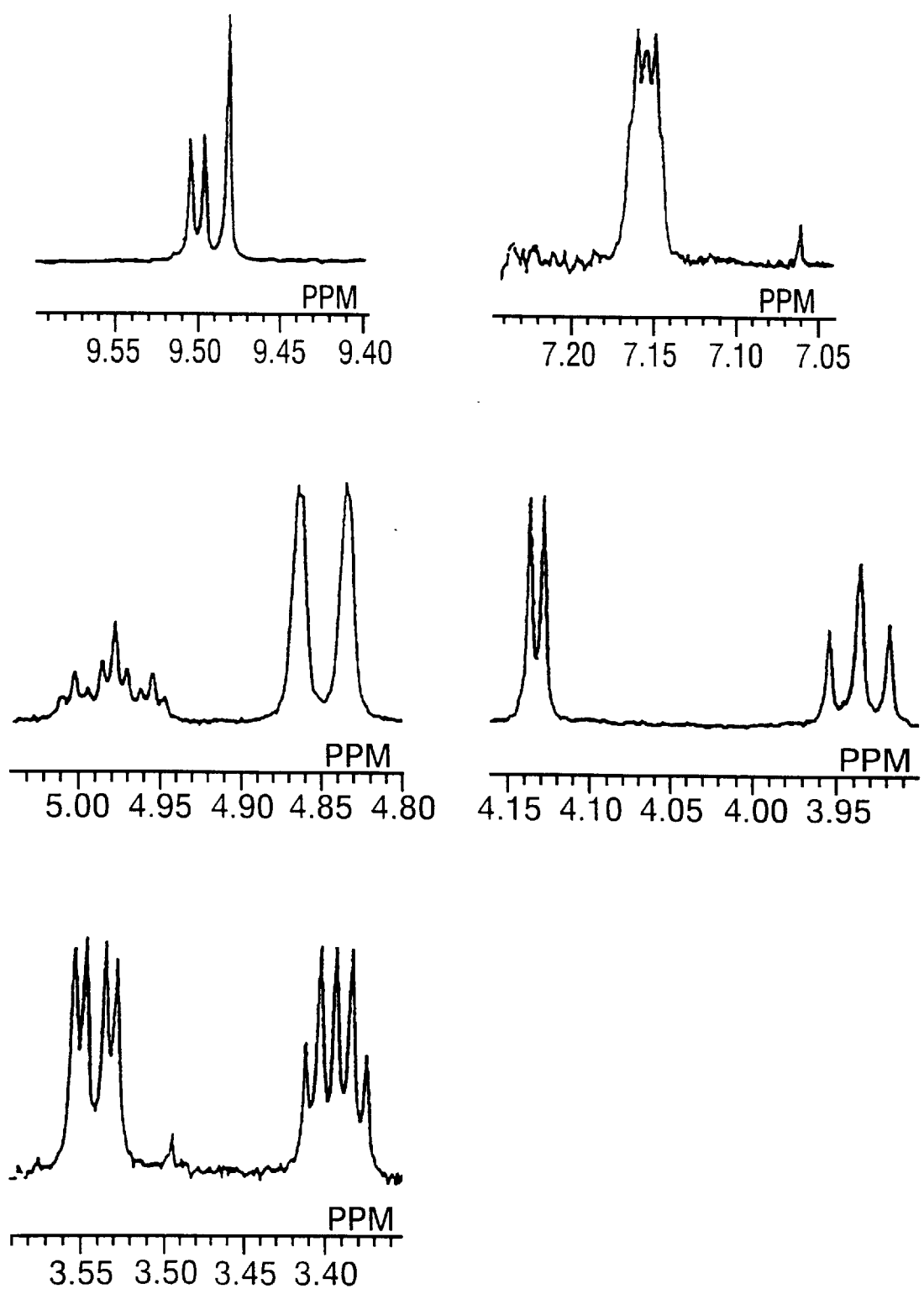
FIG. 2 shows a partial magnification of $^1$H NMR (500 MHz; CDCl$_3$) spectrum of TG101.
Figure 3:
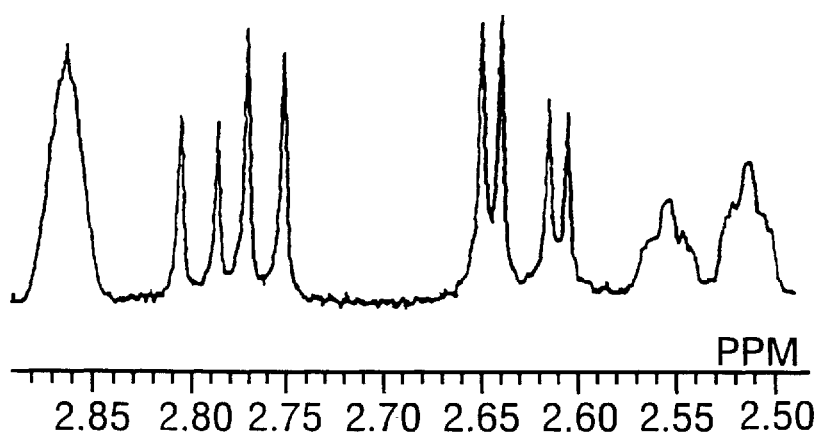
FIG. 3 shows a partial magnification of $^1$H NMR (500 MHz; CDCl$_3$) spectrum of TG101.
Figure 4:
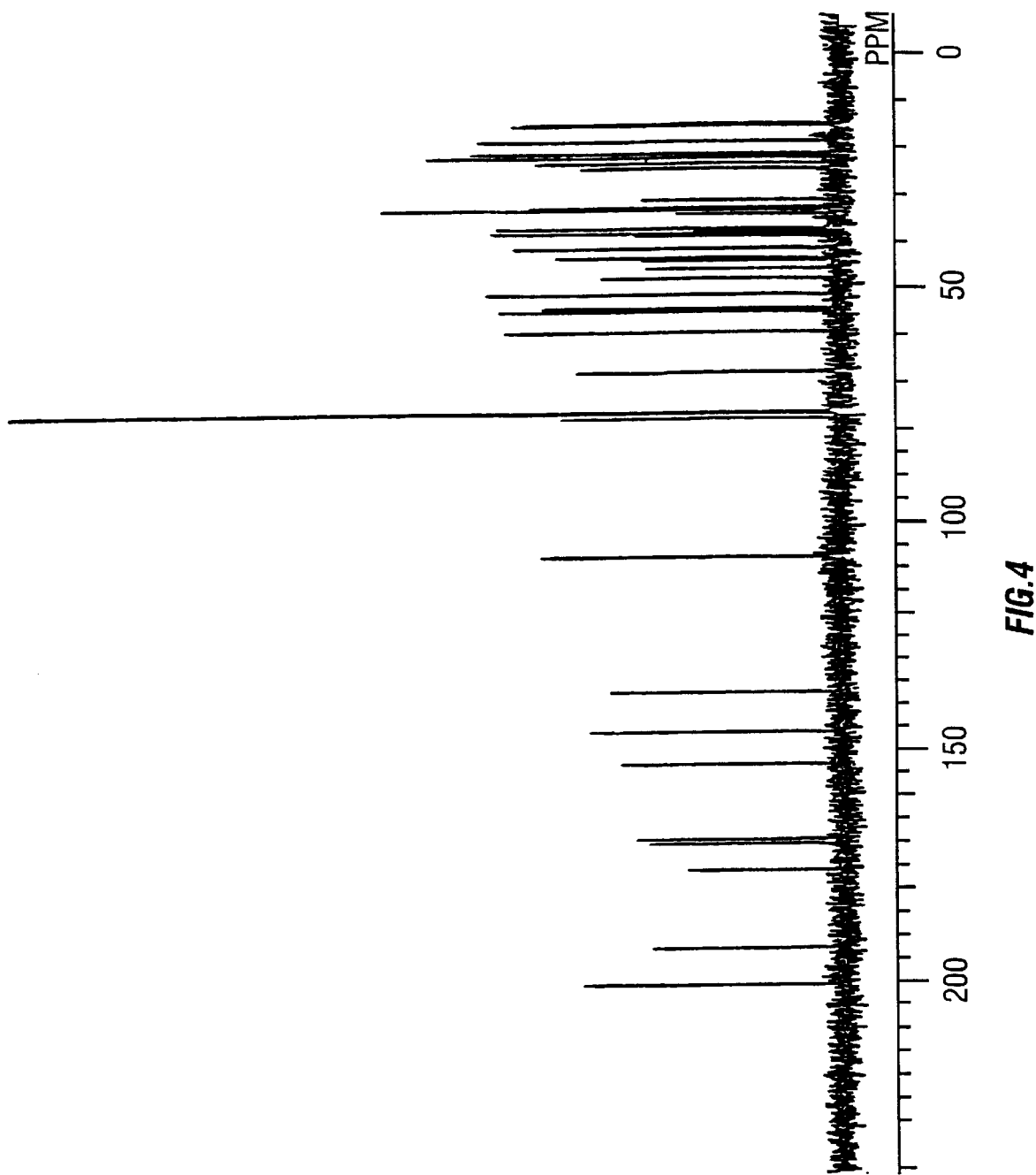
FIG. 4 shows $^{13}$C NMR (125 MHz; CDCl$_3$) spectrum of TG101.

Physico-chemical properties of TG101 are,
(1) Description: pale yellow syrup,
(2) Specific rotation: $[\alpha]_D^{24}$–20.9° (c=0.23, chloroform),
(3) Molecular weight: 642,
(4) Molecular formula: C$_{37}$H$_{54}$O$_9$,
(5) EI mass spectrum: m/z 642 (M$^+$),
(6) HREI mass spectrum: m/z 642.3748 (M$^+$: C$_{37}$H$_{54}$O$_9$), Found: 642.3768,
(7) Ultra-violet absorption spectrum (nm) $\lambda_{max}$ (MeOH) (log ε): 201 (4.12), 228 (3.98), 296 (2.96)
(8) Infrared absorption spectrum (cm$^{-1}$) $\nu_{max}$ (CHCl$_3$): 3600–2400 (br), 2925, 2850, 1750 (sh), 1720, 1680, 1640, 1460, 1440, 1380, 1360, 1300–1200 (br), 1170, 1130
(9) $^1$H NMR spectrum: as shown in FIGS. 1 to 3,
(10) $^{13}$C NMR spectrum: as shown in FIG. 4,
(11) Solubility: readily soluble in methanol, acetone, and ethyl acetate, soluble in chloroform, and slightly soluble in water
(12) R$_f$ values: silica gel thin layer chromatography on Kieselgel 60F$_{254}$ (Merck), 0.46 (chloroform/methanol=90/10)

0.17 (chloroform/ethyl acetate/methanol=15/5/1)
(13) Color reaction: positive for Ehrlich's reagent (reddish purple).

Structural Formula of TG102

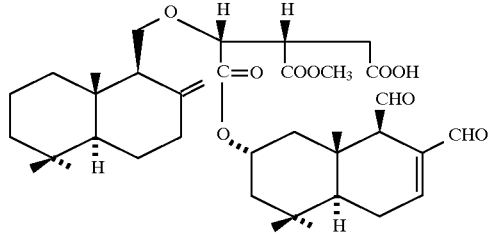

Figure 5:
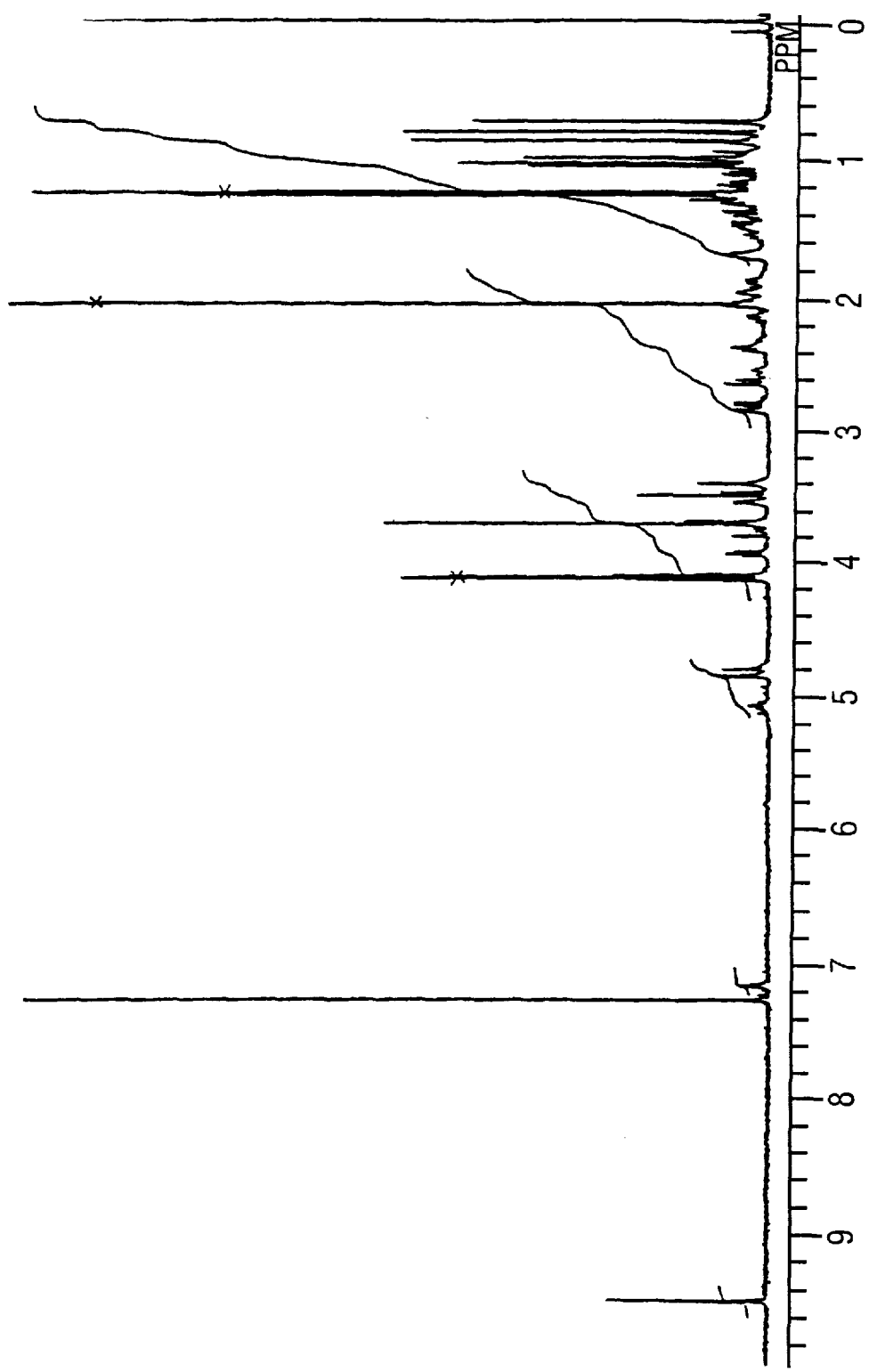
FIG. 5 shows $^1$H NMR (500 MHz; CDCl$_3$) spectrum of TG102.
Figure 6:
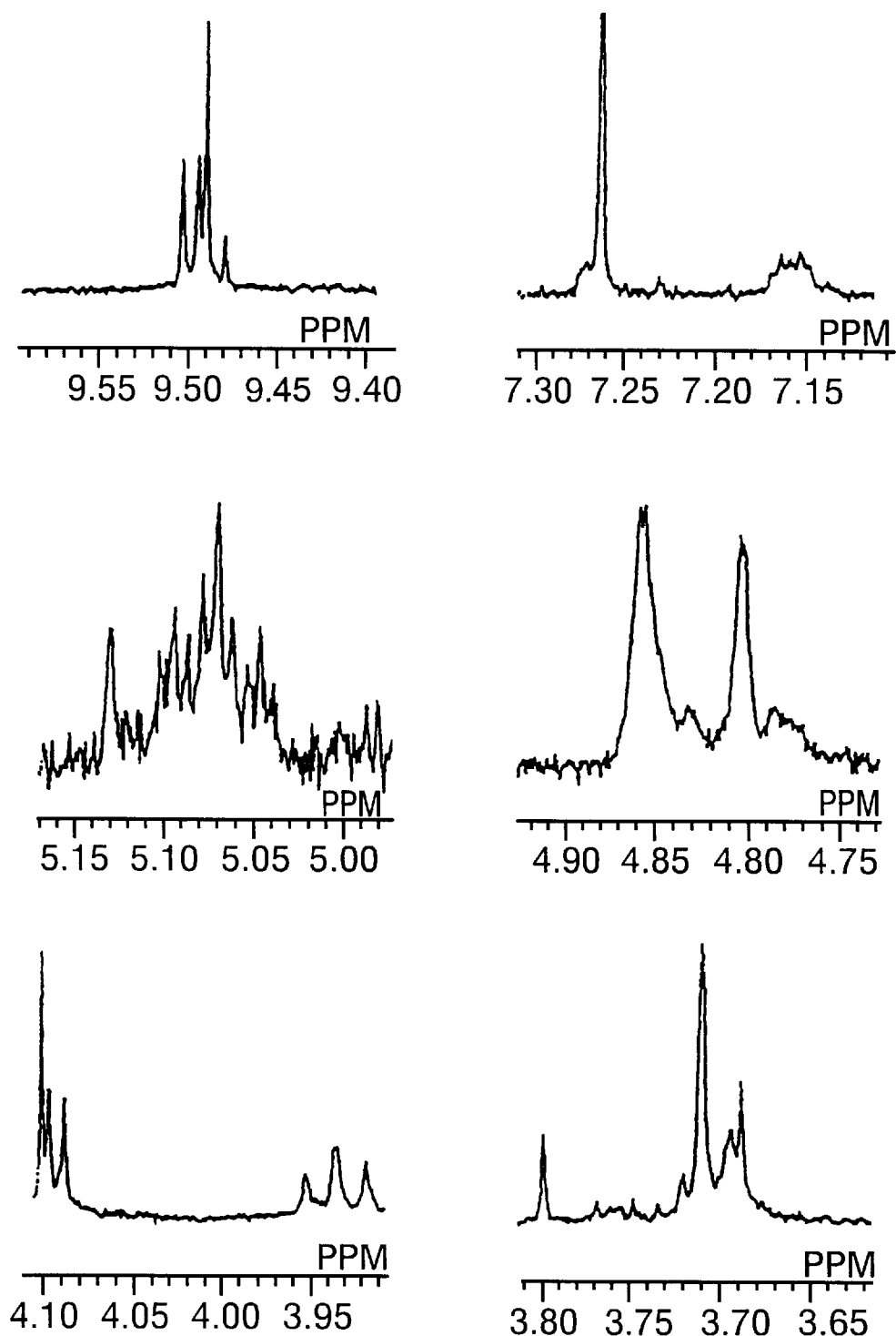
FIG. 6 shows a partial magnification of $^1$H NMR (500 MHz; CDCl$_3$) spectrum of TG102.
Figure 7:
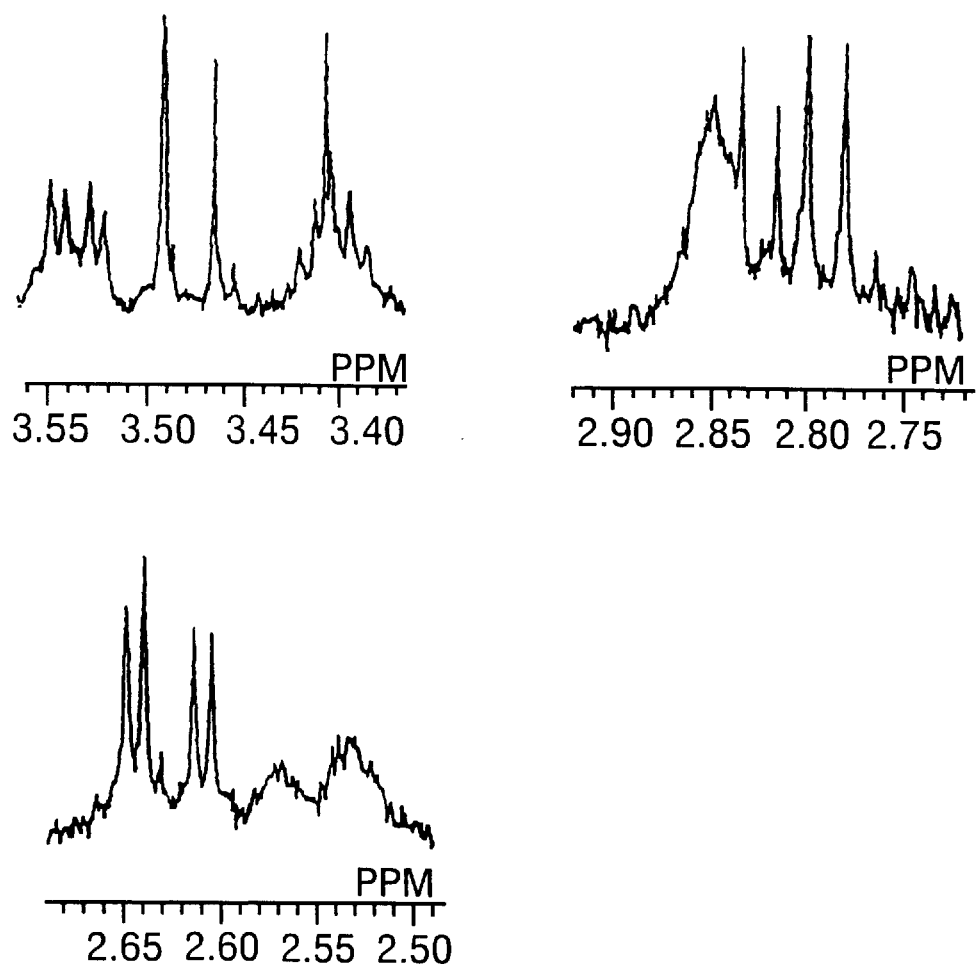
FIG. 7 shows a partial magnification of $^1$H NMR (500 MHZ; CDCl$_3$) spectrum of TG102.

Physico-chemical properties of TG102 are,
(1) Description: colorless syrup,
(2) Molecular weight: 642,
(3) Molecular formula: C$_{37}$H$_{54}$O$_9$,
(4) EI mass spectrum: m/z 642 (M$^+$),
(5) $^1$H NMR spectrum: as shown in FIGS. 5 to 7,
(6) Solubility: readily soluble in methanol, acetone, and ethyl acetate, soluble in chloroform, and slightly soluble in water,
(7) R$_f$ values: silica gel thin layer chromatography on Kieselgel 60F$_{254}$ (Merck), 0.41 (chloroform/methanol=90/10)

0.13 (chloroform/ethyl acetate/methanol=15/5/1),
(8) Color reaction: positive for Ehrlich's reagent (reddish purple)

Structural Formula of TG103

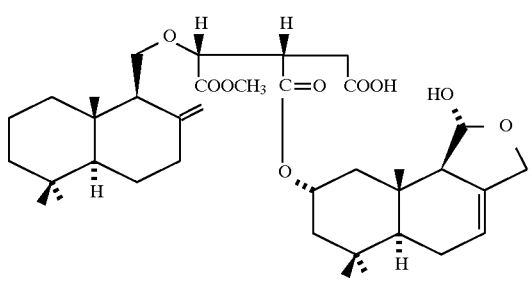

Figure 8:
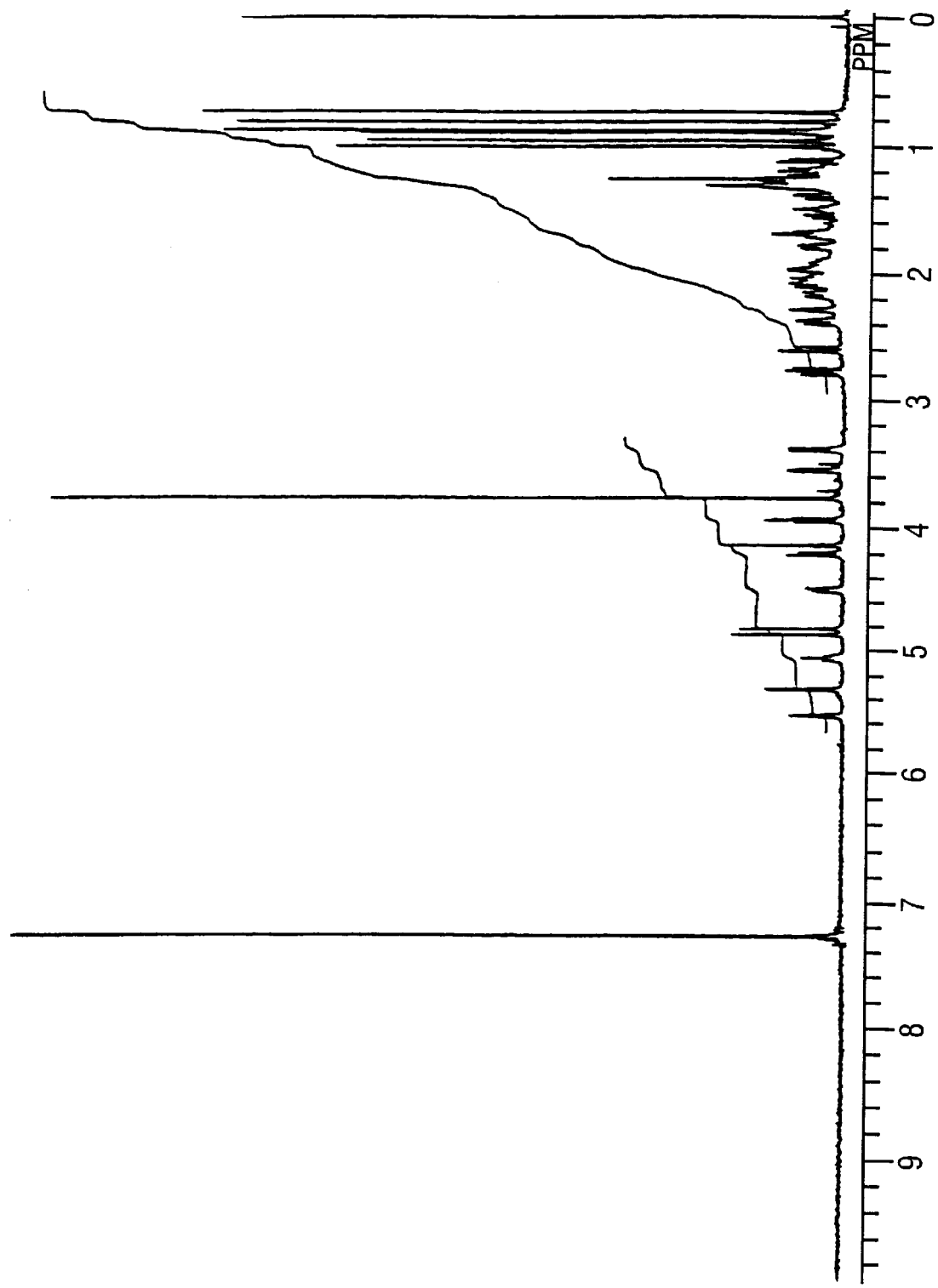
FIG. 8 shows $^1$H NMR (500 MHz; CDCl$_3$) spectrum of TG103.
Figure 9:
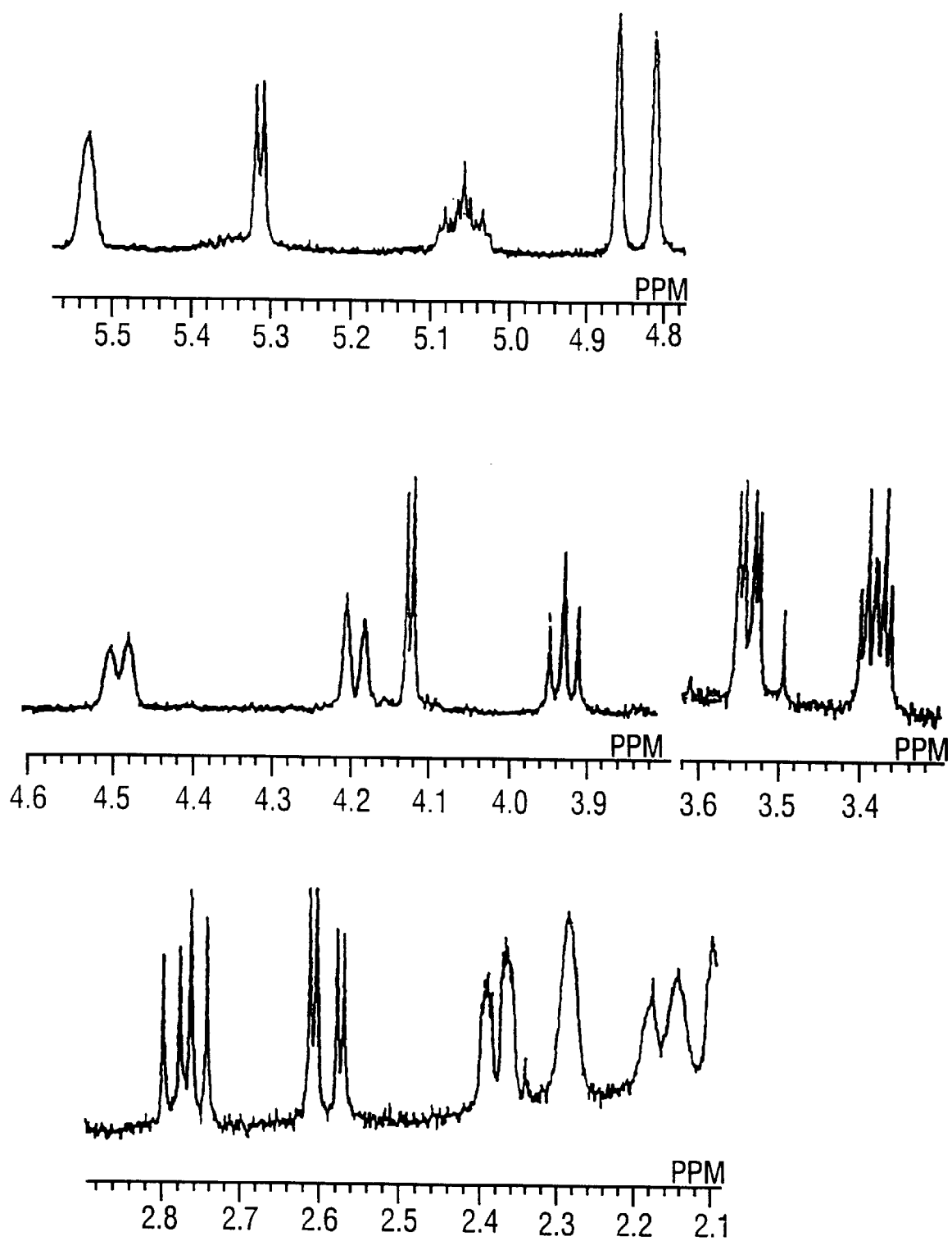
FIG. 9 shows a partial magnification of $^1$H NMR (500 MHz; CDCl$_3$) of TG103.
Figure 10:
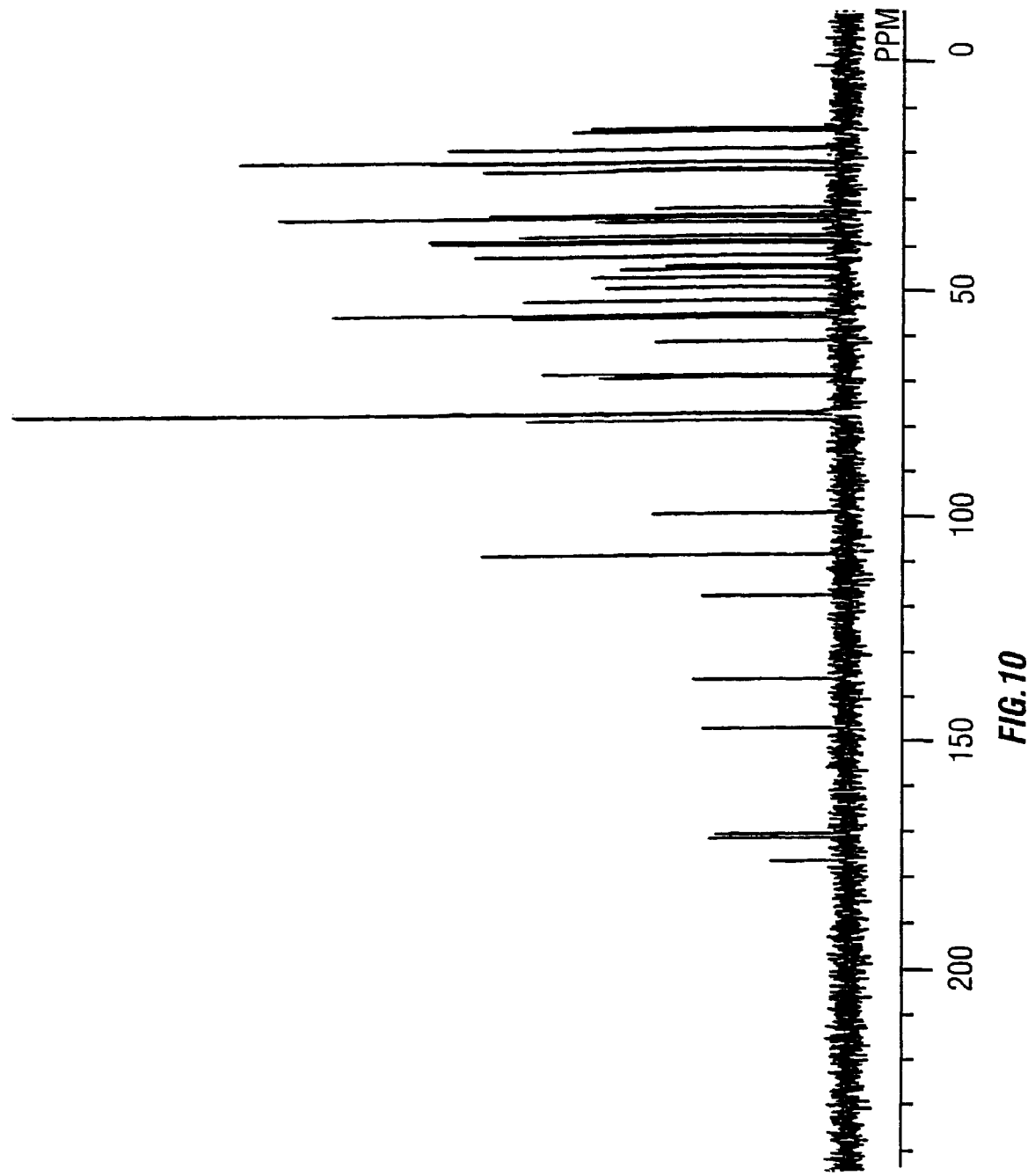
FIG. 10 shows $^{13}$C NMR (125 MHz; CDCl$_3$) spectrum of TG103.

Physico-chemical properties of TG103 are,
(1) Description: colorless syrup,
(2) Specific rotation: $[\alpha]_D^{26} +10.6°$ (c=0.17, chloroform),
(3) Molecular weight: 644,
(4) Molecular formula: $C_{37}H_{56}O_9$,
(5) FAB mass spectrum: m/z 667 [(M+Na)$^+$],
(6) HREI mass spectrum: m/z 626.3838 (M$^+$-H$_2$O: $C_{37}H_{54}O_8$), Found: 626.3819,
(7) Infrared absorption spectrum (cm$^{-1}$) $v_{max}$ (CHCl$_3$): 3625–2400 (br), 2940, 2860, 1750 (sh), 1730, 1640, 1460, 1440, 1390, 1360, 1320–1400 (br), 1130, 1010
(8) $^1$H NMR spectrum: as shown in FIGS. 8 and 9,
(9) $^{13}$C NMR spectrum: as shown in FIG. 10,
(10) Solubility: readily soluble in methanol, acetone, and ethyl acetate,
soluble in chloroform, and
slightly soluble in water,
(11) R$_f$ values: silica gel thin layer chromatography on Kieselgel 60F$_{254}$ (Merck),
0.29 (chloroform/methanol=90/10)
0.07 (chloroform/ethyl acetate/methanol=15/5/1),
(12) Color reaction: positive for Ehrlich's reagent (reddish purple).

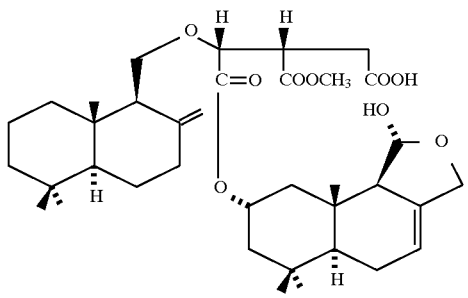

Figure 11:
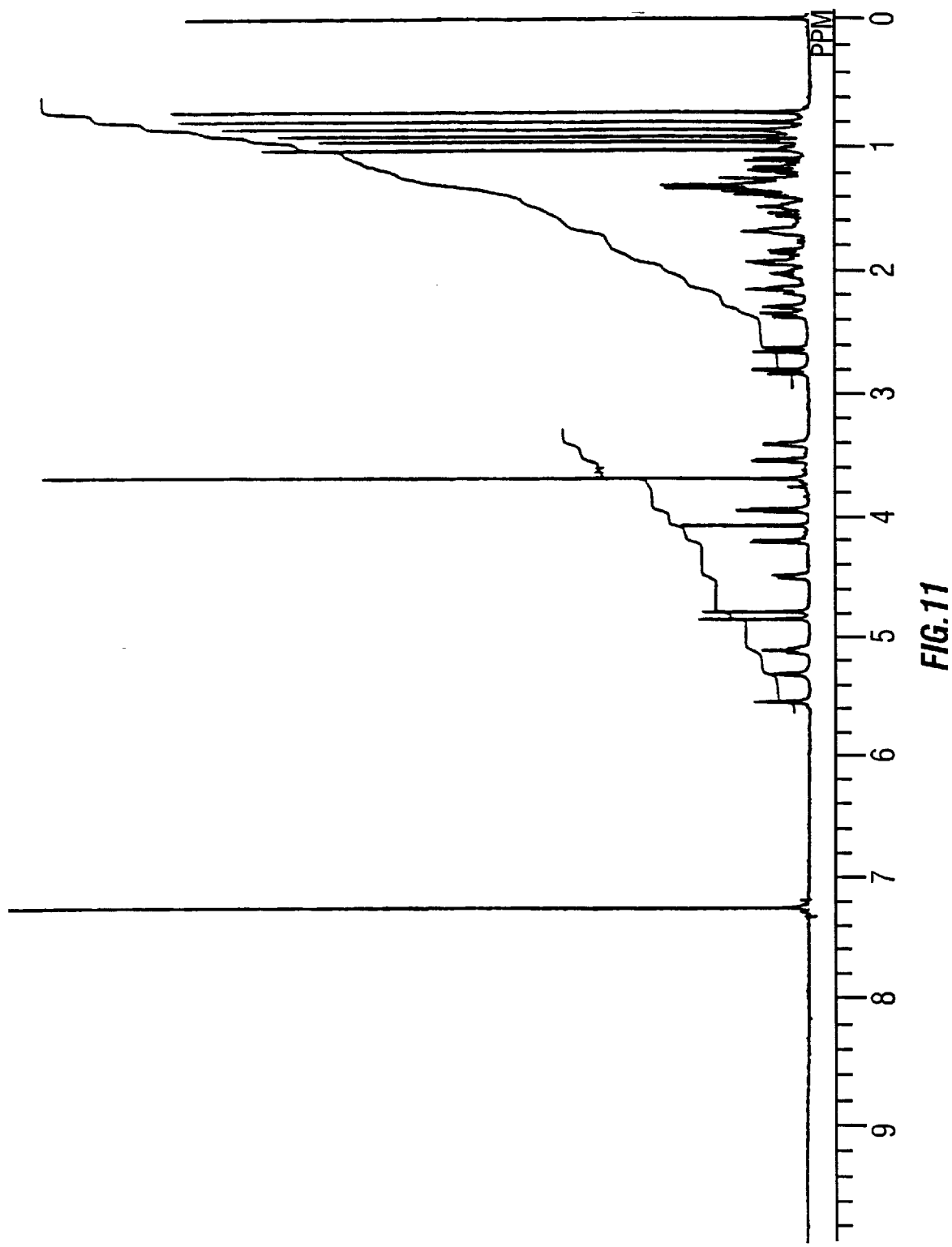
FIG. 11 shows $^1$H NMR (500 MHz; CDCl$_3$) spectrum of TG104.
Figure 12:
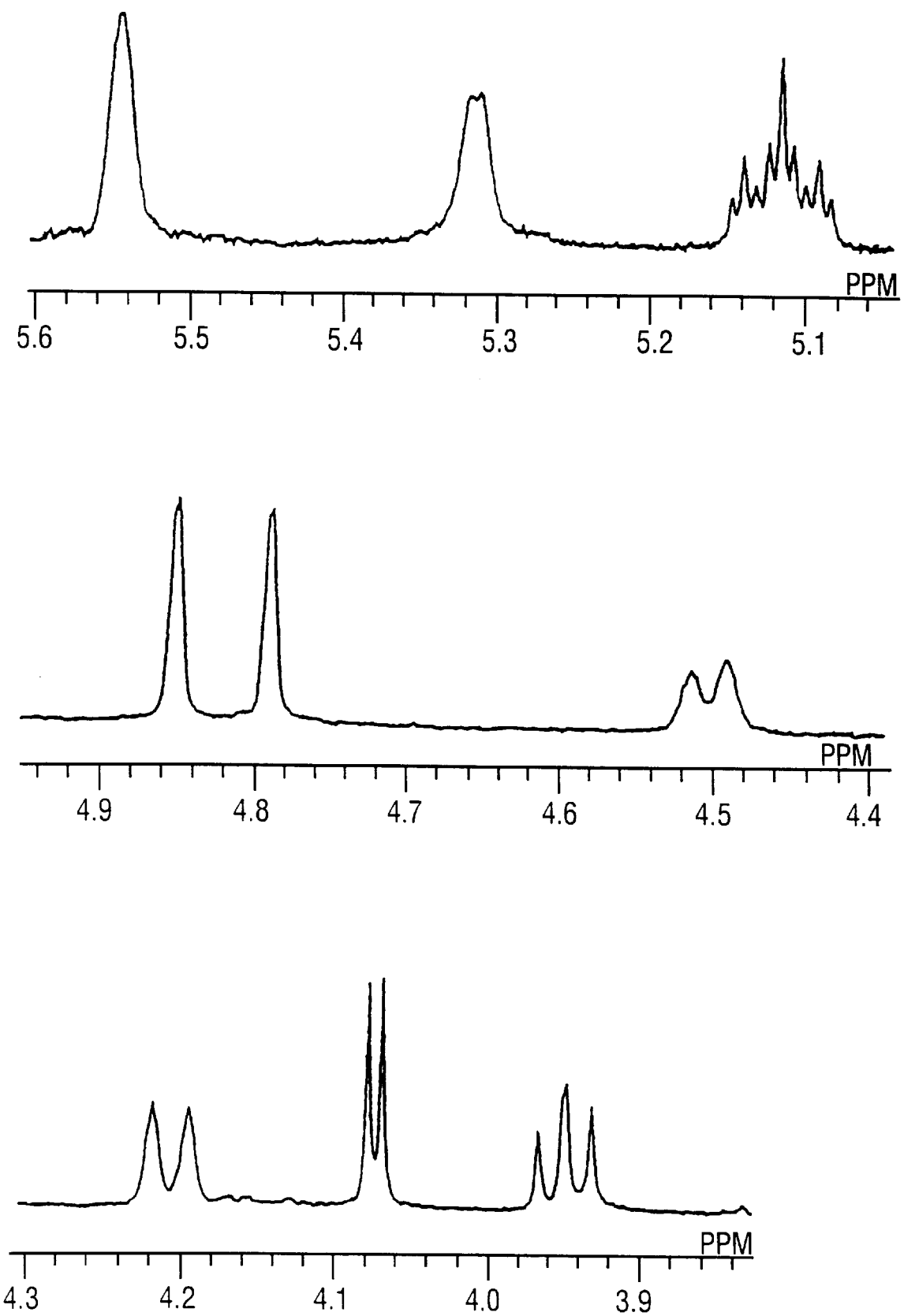
FIG. 12 shows a partial magnification of $^1$H NMR (500 MHz; CDCl$_3$) spectrum of TG104.
Figure 13:
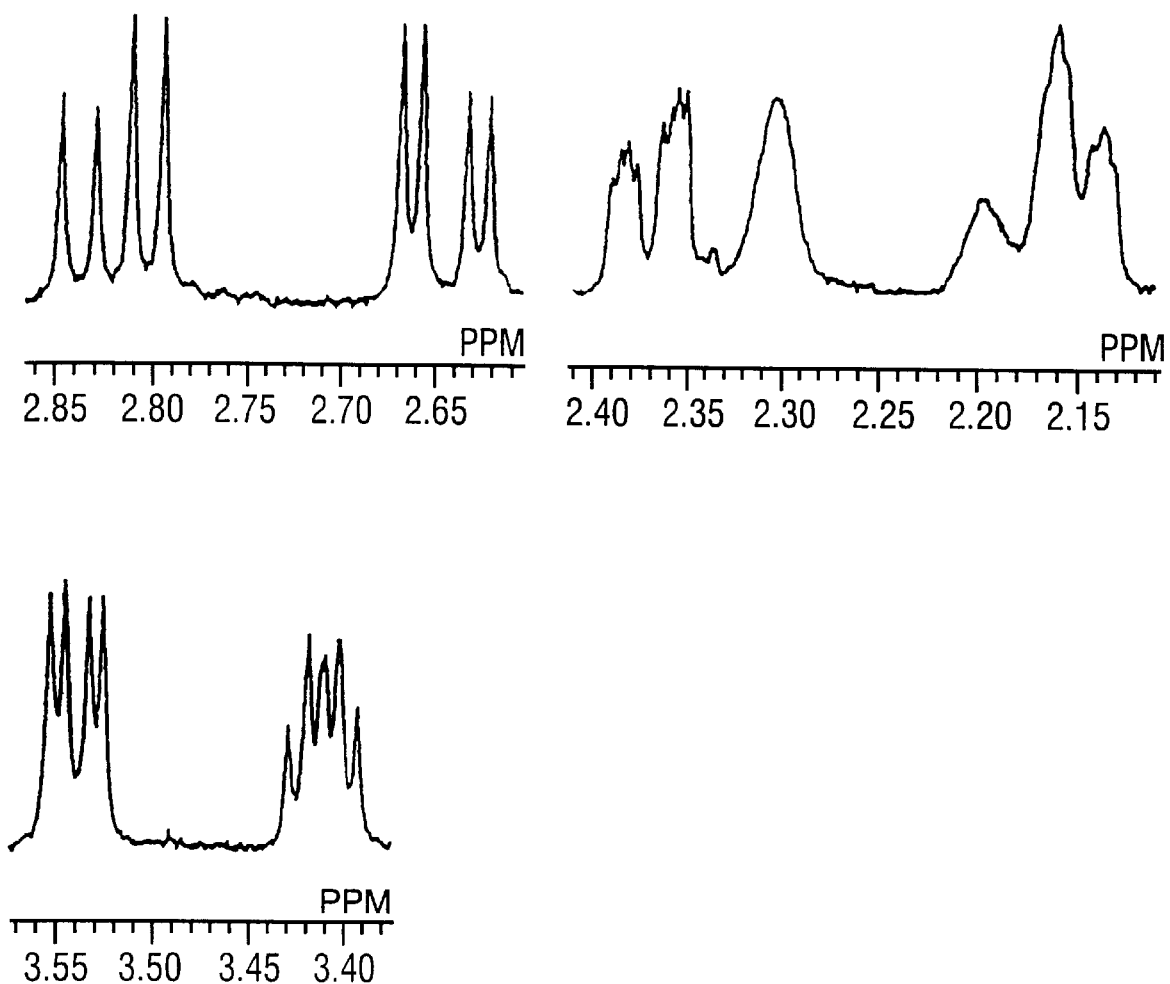
FIG. 13 shows a partial magnification of $^1$H NMR (500 MHz; CDCl$_3$) spectrum of TG104.

Physico-chemical properties of TG104 are,
(1) Description: colorless syrup,
(2) Specific rotation: $[\alpha]_D^{24} +25.6°$ (c=0.36, chloroform),
(3) Molecular weight: 644,
(4) Molecular formula: $C_{37}H_{56}O_9$,
(5) FAB mass spectrum: m/z 667 [(M+Na)$^+$],
(6) HREI mass spectrum: m/z 626.3859 (M$^+$-H$_2$O: $C_{37}H_{54}O_8$), Found: 626.3819,
(7) Infrared absorption spectrum (cm$^{-1}$) $v_{max}$ (CHCl$_3$): 3625–2400 (br), 2930, 2850, 1740, 1720 (sh), 1640, 1460, 1440, 1390, 1360, 1340–1150 (br), 1130, 1010
(8) $^1$H NMR spectrum: as shown in FIGS. 11 to 13,
(9) Solubility: readily soluble in methanol, acetone and ethyl acetate,
soluble in chloroform,
slightly soluble in water,

(10) R$_f$ values: silica gel thin layer chromatography on Kieselgel 60F$_{254}$ (Merck),
0.24 (chloroform/methanol=90/10)
0.03 (chloroform/ethyl acetate/methanol=15/5/1),
(11) Color reaction: positive for Ehrlich's reagent (reddish purple)

Example 2

Biological Assay

Out of the compounds obtained as described above, TG101 and TG103 were assayed for their anti-microbial activity in vitro against *Candida albicans*, *Cryptococcus neoformans*, *Aspergillus nigar* and *Aspergillus fumigatus* as fungi to be tested, confirming their anti-fungal activities. In the following, examples of anti-fungal assays are described.

In the assay standard microbial strains supplied from Research Center for Eumyceta and Mycosis, Teikyo University, Japan, were used as the test fungi, and Yeast Morphology Ager (DIFCO) was used as the medium for the drug sensitivity assays.

Firstly, the given fungus was smeared on the potato-dextrose agar media (Nissui Seiyaku) slants, incubated at 30° C. for 1 day (for *Candida albicans* and *Cryptococcus neoformans*) or for 4 days (for *Aspergillus nigar* and *Aspergillus fumigatus*), and then the fungus grown on the slant was washed out with a sterilized physiological salt solution containing 0.1% Tween 80. The washed out fungus was passed through a filter with 15 μm bores, and, after the number of fungus colonies were counted on the blood cell counting plate, a suspension containing 10$^5$ CFU/ml of fungus was prepared to be used as the inoculation solution. After this solution (0.02 ml) was inoculated to Yeast Morphology Ager containing a drug at concentrations in a serial double dilution, it was cultured at 30° C. for either 1 day or 4 days.

Anti-fungal effects were estimated with naked eyes, and the minimal inhibitory concentration (MIC) was defined as the drug concentration at which the fugal growth was evidently inhibited as compared with that in the control medium not containing the drug. Table 1 shows the anti-fungal activity of TG101 and TG103 determined by the above assays.

TABLE 1

| Fungus strain/drug | MIC (μg/ml) | |
|---|---|---|
| | TG101 | TG103 |
| *C. albicans* TIMM1623 | 100 | 100 |
| *C. neoformans* TIMM0354 | 50 | 50 |
| *A. niger* TIMM0113 | 50 | 100 |
| *A. fumigatus* TIMM0063 | 50 | 25 |

Example 3

Isolation of Cryptoporic acid A (CA-A)

Fruit bodies (678 g) of Hounen-take were harvested in Makabe-cho, Ibaraki Prefecture, Japan, in September, 1995, dried at room temperature, and then pulverized with a mixer. Pulverized fruit bodies (310 g) were extracted by immersing them in ethyl acetate (4 l) at room temperature for 1 day. The same extraction procedure was repeated twice, and, after the extracts were analyzed for the ingredients by thin layer chromatography, they were combined.

Then, this combined ethyl acetate extract (11 g) was subjected to silica gel column chromatography (silica gel, 110 g; 4.5 cm ID), and eluted with chloroform/ethyl acetate and chloroform/methanol. Of the six fractions thus obtained, the fraction (4.3 g) eluted with chloroform/methanol (90/10) was subjected to column chromatography on 10% water-containing silica gel (43 g: 3.0 cm ID, eluent: chloroform/methanol=99/1 to 95/5). Then, fractions (1.9 g) containing TG101 and TG102 (eluted with chloroform/methanol=98/2 to 97/3) were further fractionated by chromatography on a Sephadex LH-20 column (225 cc: 2.0 cm ID, eluent: methanol). Those fractions containing TG101 and TG102 were concentrated in vacuo to dry, and a portion (560 mg) of the residue was subjected repeatedly to a column (60 cc: 2.0 cm ID, eluent: water/methanol=25/75 to 0/100) chromatography on Cosmosyl 75$C_{18}$-OPN (Nakalai Tesue, Japan) to obtain cryptoporic acid A (CA-A, 31.6 mg) as white powder.

Figure 14:
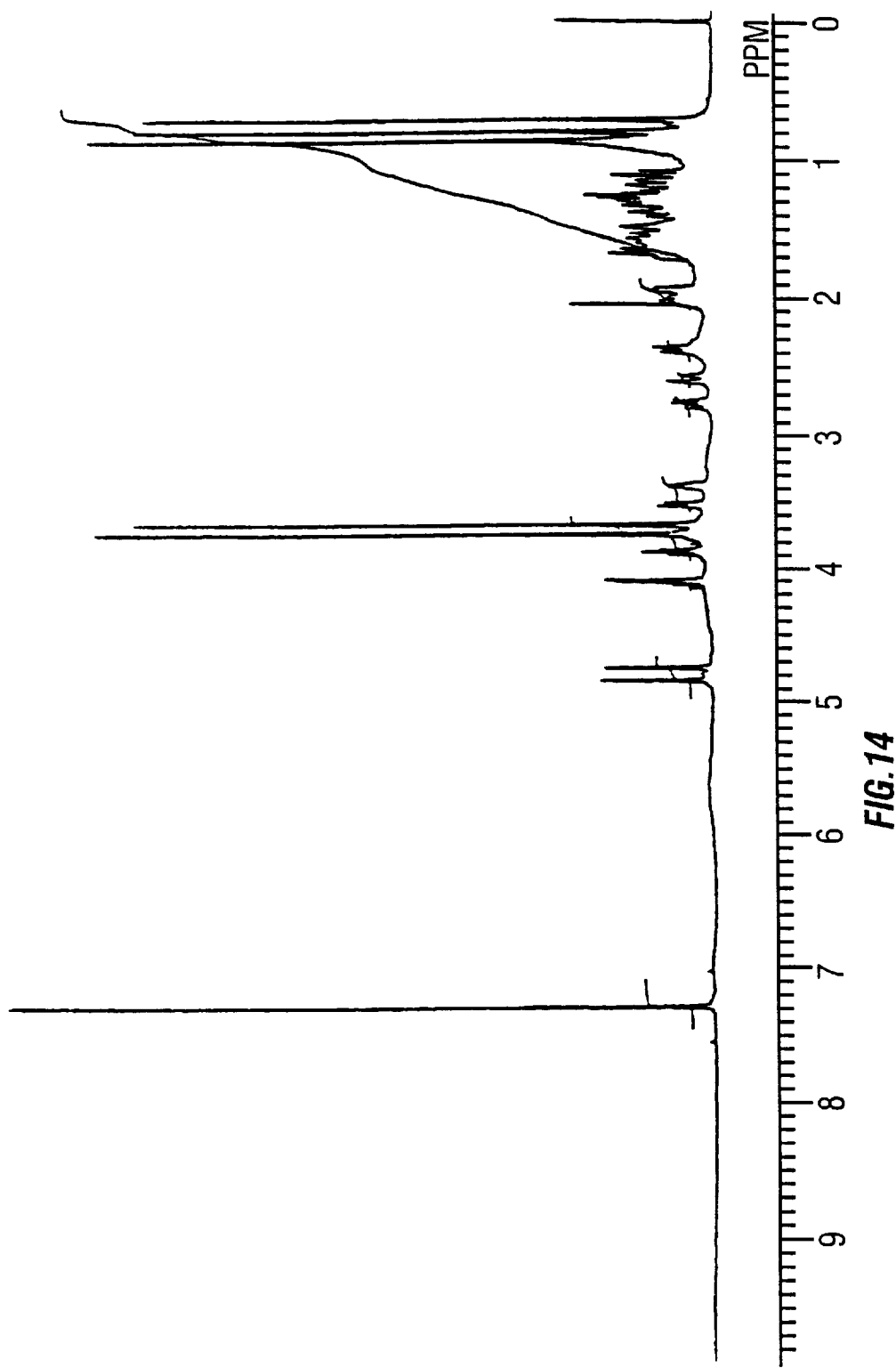
FIG. 14 shows $^1$H NMR (500 MHz; CDCl$_3$) spectrum of CA-A.
Figure 15:
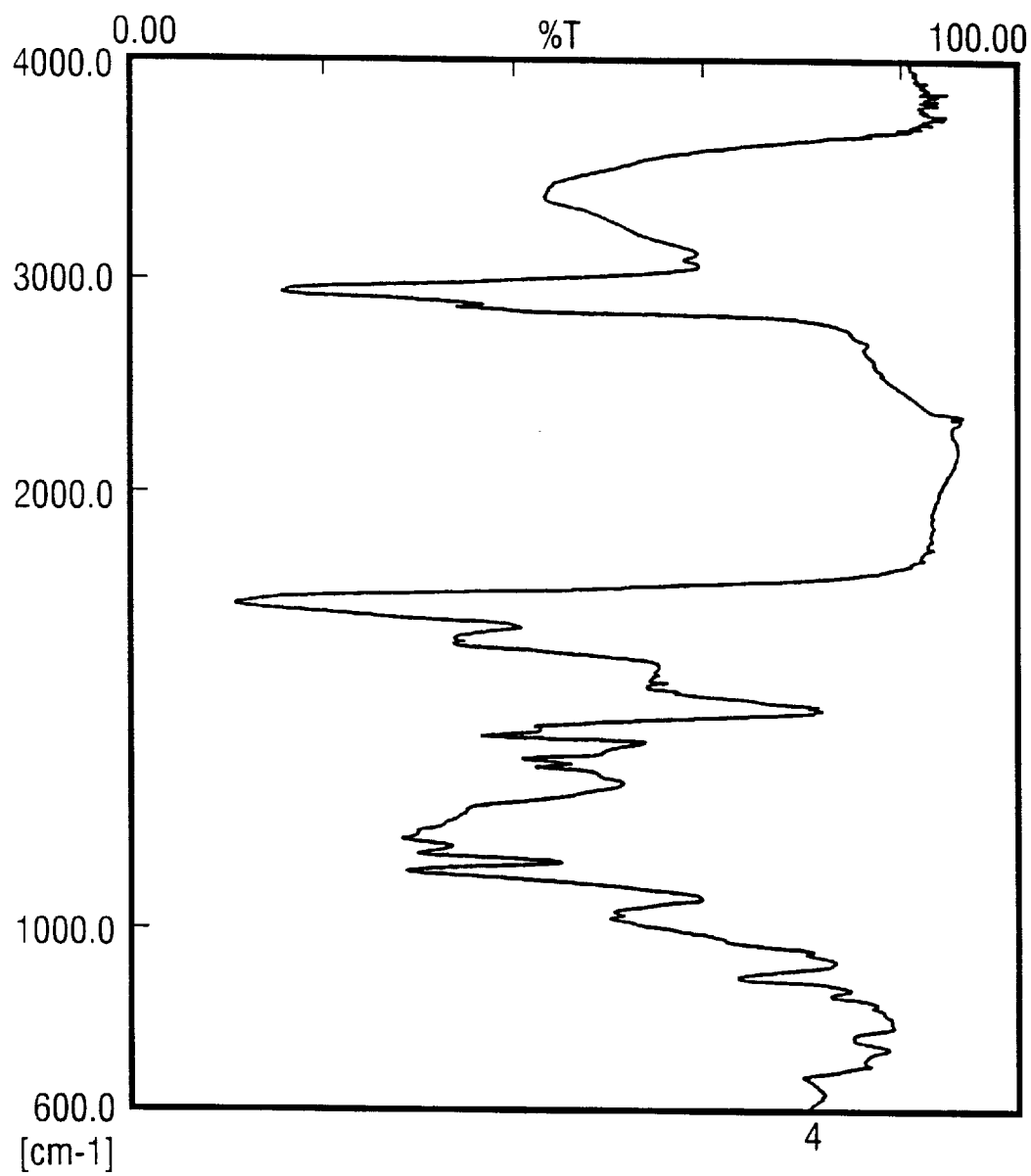
FIG. 15 shows an infrared absorption spectrum (KBr) of CA-A.

A 500 MHz $^1$H NMR spectrum (CDCl$_3$) of CA-A is shown in FIG. 14, and its infrared absorption spectrum (KBr) in FIG. 15.

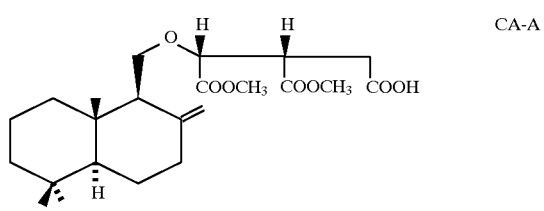

CA-A

Example 4

Syntheses of Derivatives

Synthesis of Oxidation Product of TG103 (TG103-OX)

To a solution of TG103 (120 mg: 0.2 mmol) in acetone (2 ml) were added a small amount of celite and then Jones reagent (100 μl) dropwise while stirring over ice. After stirring for 30 min at the same temperature, isopropanol (0.5 ml) was added to the reaction mixture to decompose the excessive reagent. To the reaction solution was added ether (20 ml), and precipitates formed were removed by filtration. After the filtrate was washed with water, the ether layer was dried over magnesium sulfate, and then the solvent was distilled off. Purification of the residue thus obtained by silica gel column chromatography (eluent: chloroform/methanol) yielded the oxidation derivative (80 mg) as white powder.

Figure 16:
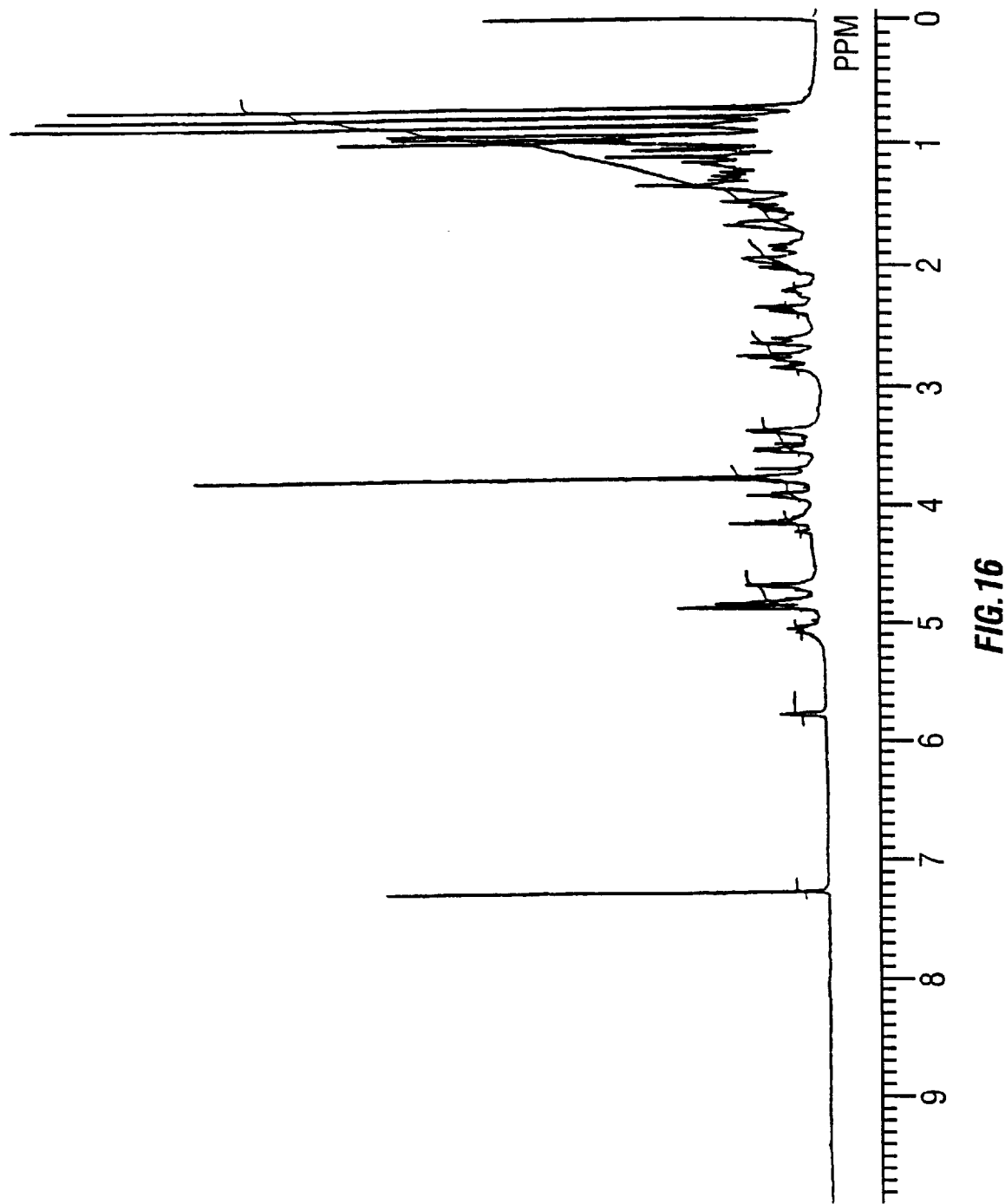
FIG. 16 shows $^1$H NMR (500 MHz; CDCl$_3$) spectrum of TG103-OX.
Figure 17:
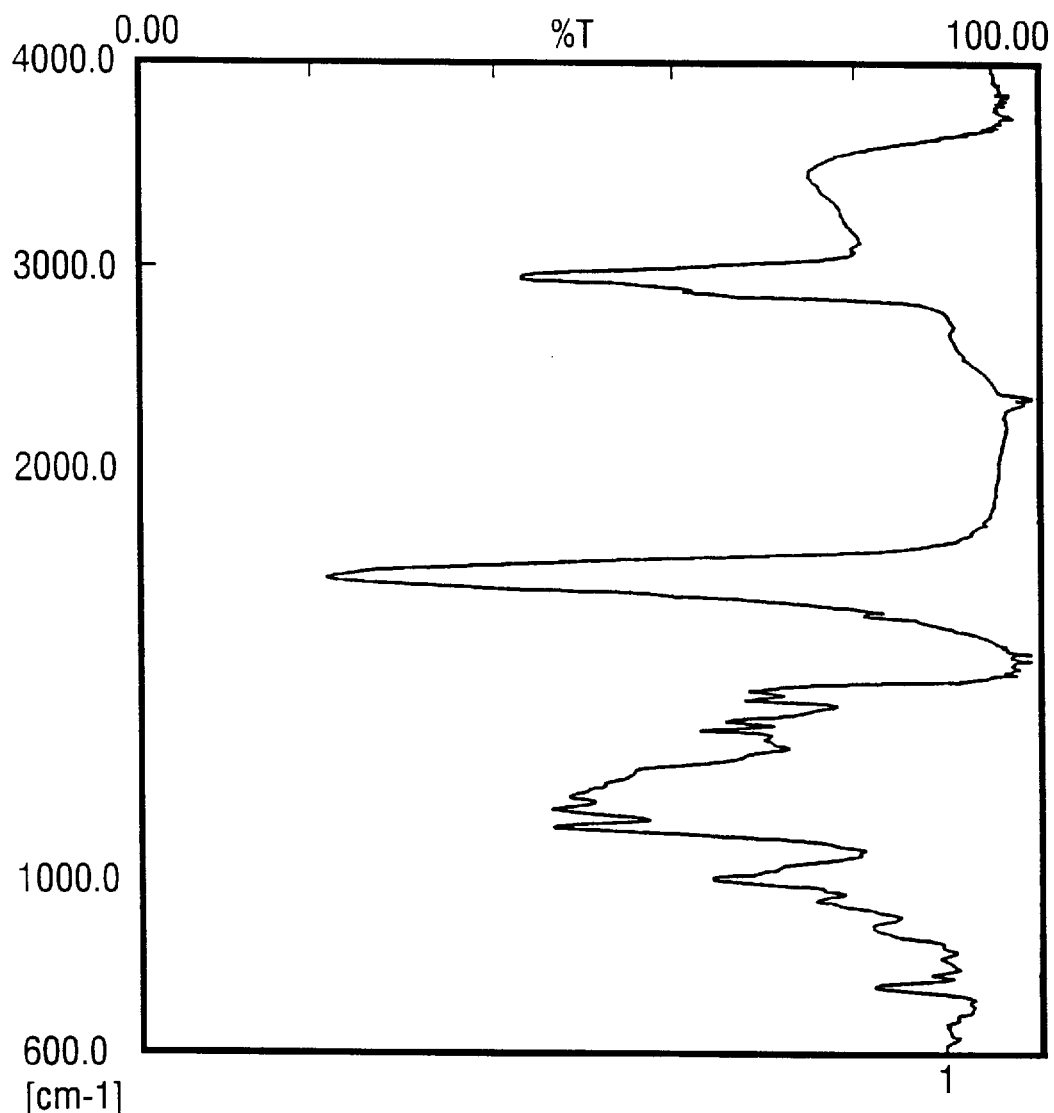
FIG. 17 shows an infrared absorption spectrum (KBr) of TG103-OX.

A $^1$H NMR spectrum (500 MHz, CDCl$_3$) of TG103-OX is shown in FIG. 16, and its infrared absorption spectrum (KBr) in FIG. 17.

Example 5

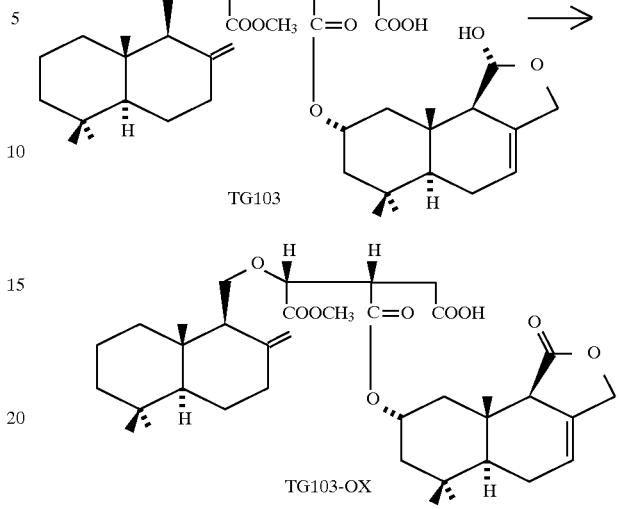

Synthesis of Cryptoporic Acid H (CA-H)

To a solution of TG103 (32 mg: 0.05 mmol) in ethanol (1 ml) was added 1N sodium hydroxide solution (1 ml), and the mixture was refluxed for 3 h. After the reaction was over, the reaction solution was diluted with water (4 ml), and washed with ethyl acetate (10 ml each) twice. Then, the aqueous layer was acidified with 1N HCl, and extracted with ethyl acetate (10 ml each) twice. Combined extracts were successively washed with water and saturated sodium chloride solution, and then dried over magnesium sulfate. After the solvent was distilled off, the residue was purified by ODS column chromatography (COSMOSIL 75$C_{18}$ OPN: 2.0 cm ID, eluent: water/methanol=30/70 to 0/100) to yield cryptoporic acid H (13 mg) as white powder.

Figure 18:
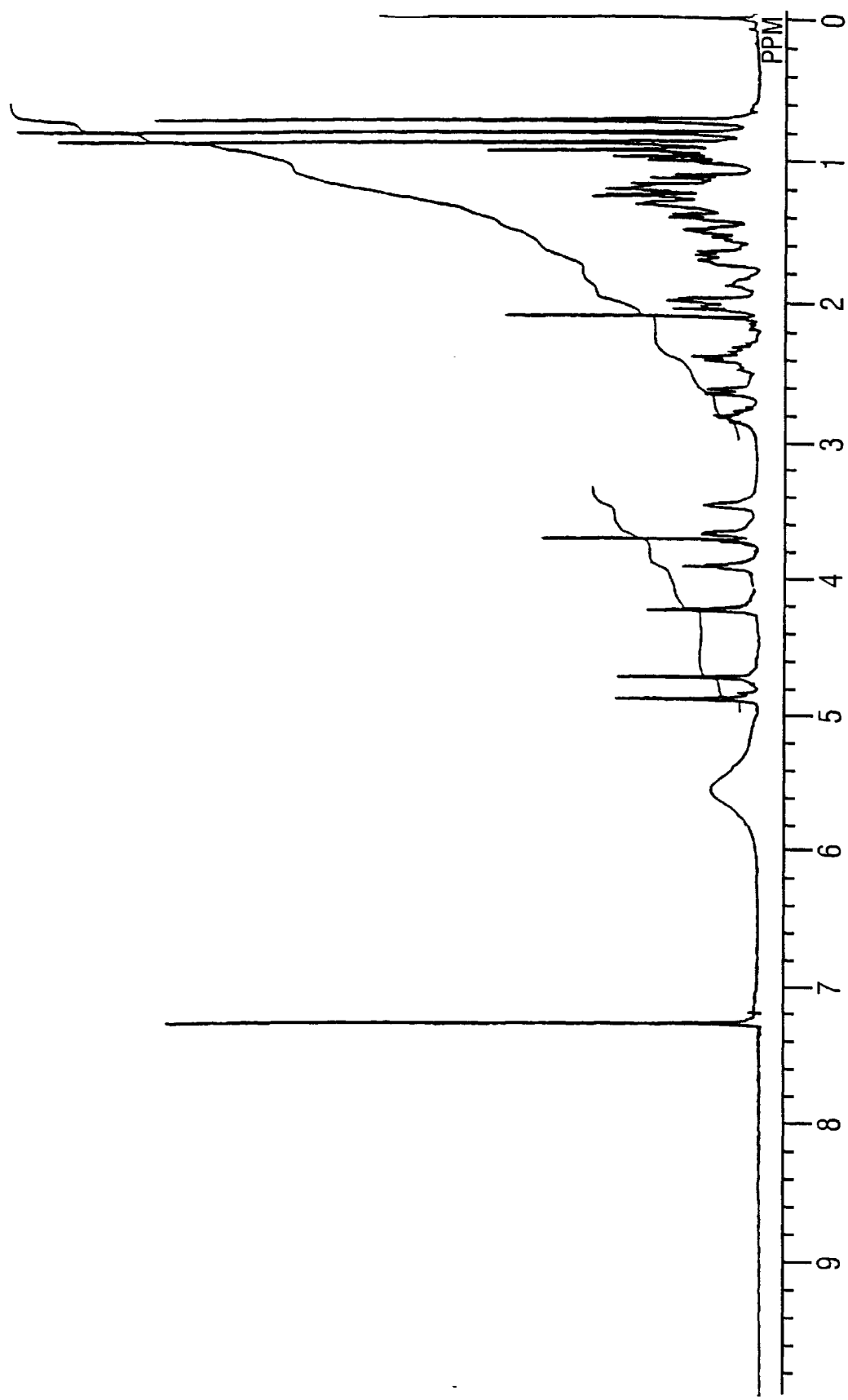
FIG. 18 shows $^1$H NMR (500 MHz; CDCl$_3$) spectrum of CA-H.
Figure 19:
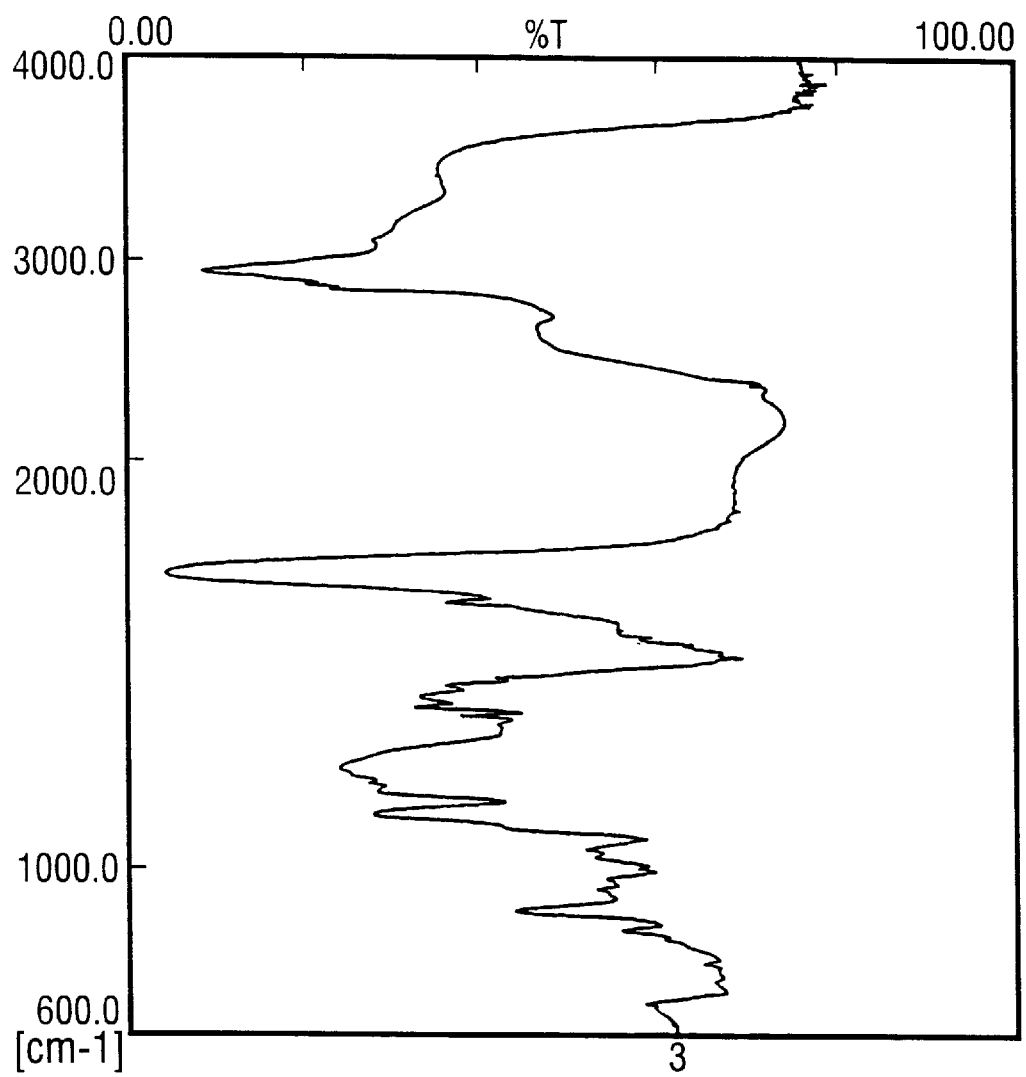
FIG. 19 shows an infrared absorption spectrum (KBr) of CA-H.

A $^1$H NMR spectrum 500 MHz (CDCl$_3$) of CA-H is shown in FIG. 18, and its infrared absorption spectrum (KBr) in FIG. 19.

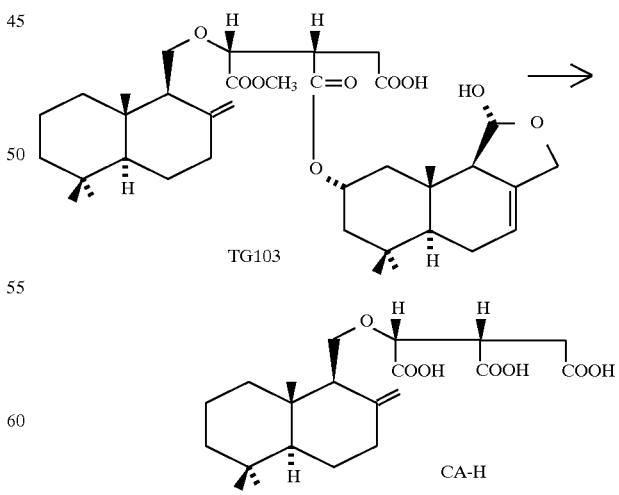

MIC assay of cryptoporic acid H was carried out by the similar procedure as described above. The results are shown in Table 2.

13

TABLE 2

| Fungus strain/drug | MIC Cryptoporic acid H |
|---|---|
| *Candida albicans* TIMM1623 | 200 µg/ml |
| *Saccharomyces cerevisiae* JCM2216 | 200 µg/ml |
| *Aspergillus fumigatus* TIMM0063 | 200 µg/ml |
| *Aspergillus niger* TIMM0113 | 200 µg/ml |

Example 6

Synthesis of the Trimethyl Ester of Cryptoporic Acid H (CA-H-Me)

To a solution of TG101 (19 mg: 0.05 mmol) in ethanol (1 ml) was added 1N sodium hydroxide solution (1 ml), and the reaction solution was refluxed for 2 h. After the reaction was over, the reaction solution was diluted with water (3 ml), and washed with ethyl acetate (5 ml each) twice. Then, the aqueous layer was acidified with 1N HCl, and further extracted with ethyl acetate (5 ml each) twice. Combined extracts were successively washed with water and saturated sodium chloride solution. After dried over magnesium sulfate, the solvent was distilled off. The residue thus obtained was dissolved in methanol, and treated with diazomethane in ether. The solvents were distilled off from the reaction solution, and the residue was purified by silica gel column chromatography (eluent: n-hexane/ethyl acetate) to obtain the trimethyl ester derivative of CA-H (CA-H-Me) as white powder (7 mg).

Figure 20:
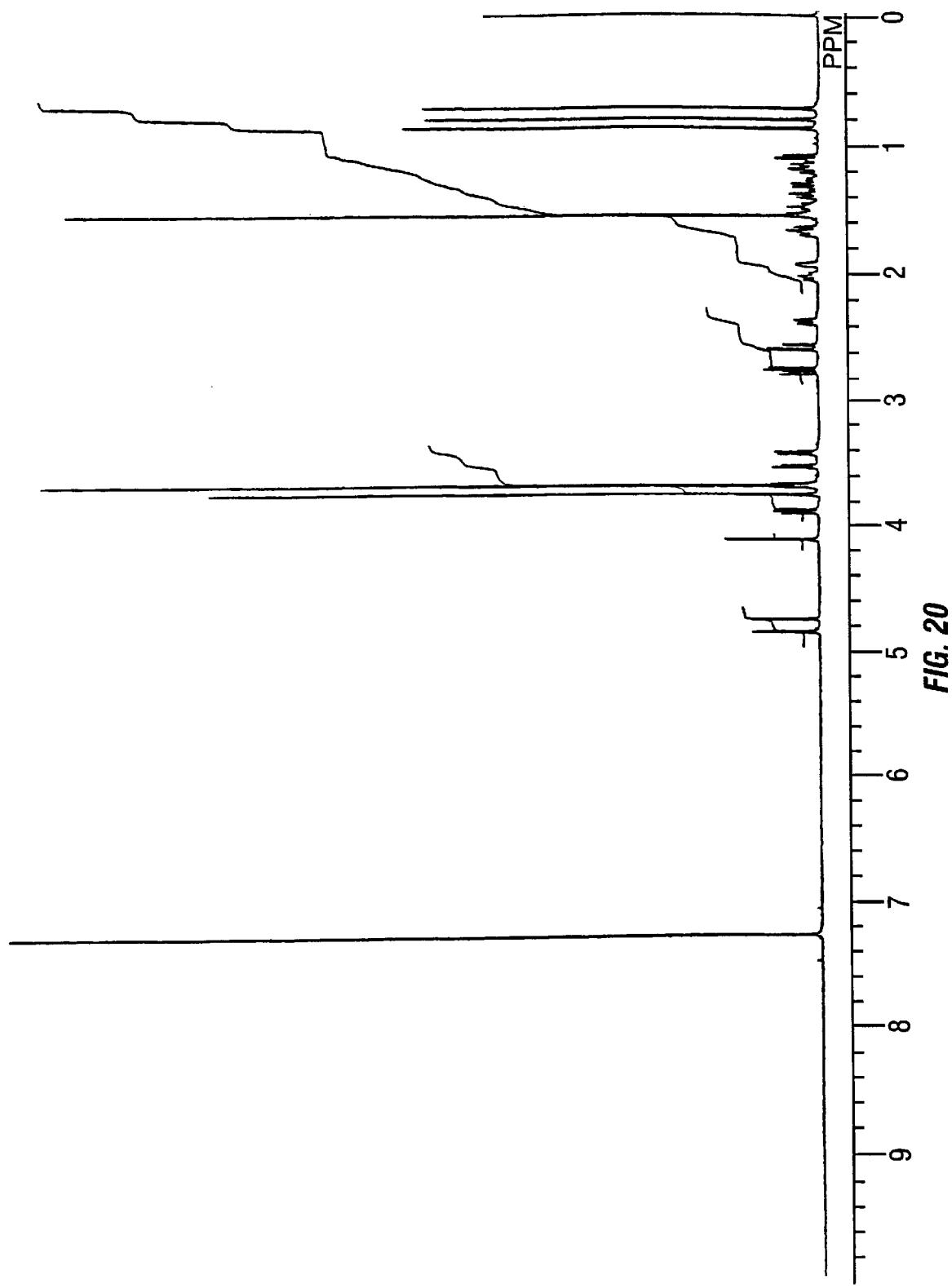
FIG. 20 shows $^1$H NMR (500 MHz; CDCl$_3$) spectrum of CA-H-Me.
Figure 21:
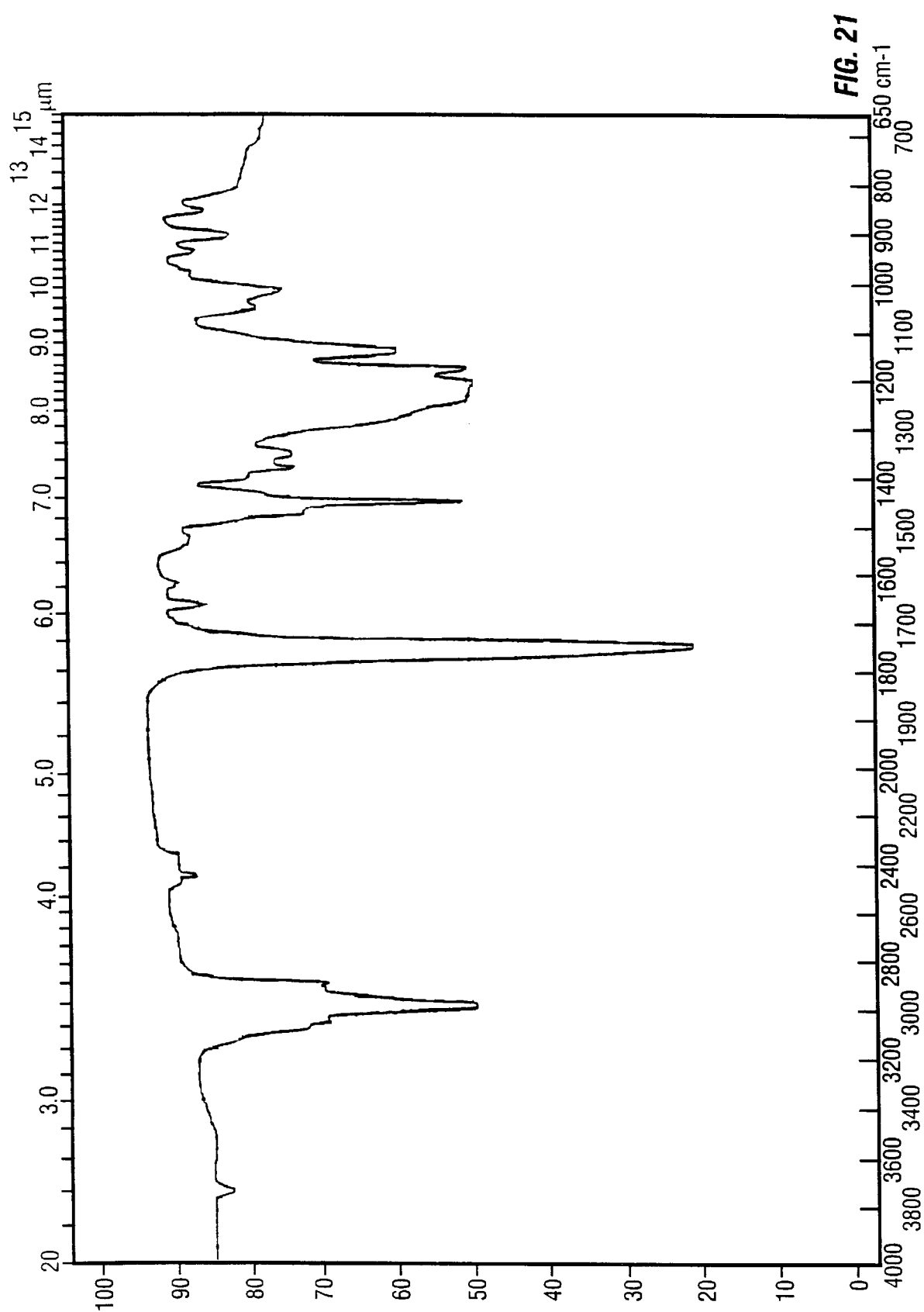
FIG. 21 shows an infrared absorption spectrum (KBr) of CA-H-Me.

A $^1$H NMR spectrum (500 MHz) (CDCl$_3$) of CA-H-Me is shown in FIG. 20, and its infrared absorption spectrum (KBr) shown in FIG. 21.

Example 7

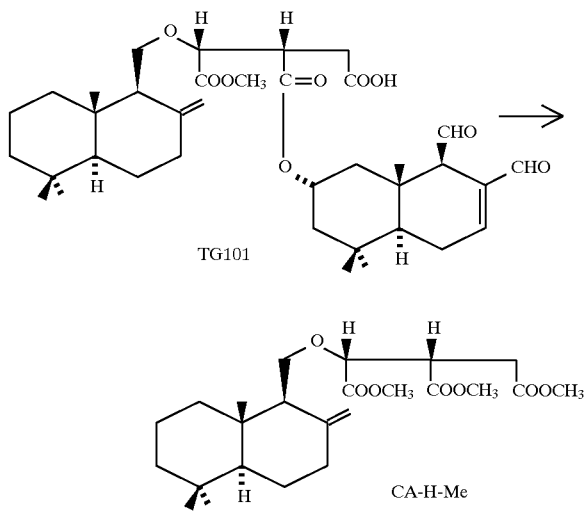

Methylation of TG101 and TG103

To a solution of TG101 (640 mg: 1 mmol) in ether/methanol (4 ml/2 ml) was added a 10% solution of trimethylsilyl diazomethane in n-hexane (1.8 ml) dropwise while stirring over ice, and the reaction solution was stirred at the same temperature for 30 min. After the solvent was distilled off, the residue was purified by silica gel column chromatography (20 g: 2.0 cm ID, eluent: n-hexane-ethyl acetate) to obtain the methyl ester derivative of TG101 (537 mg) as white powder.

14

Figure 22:
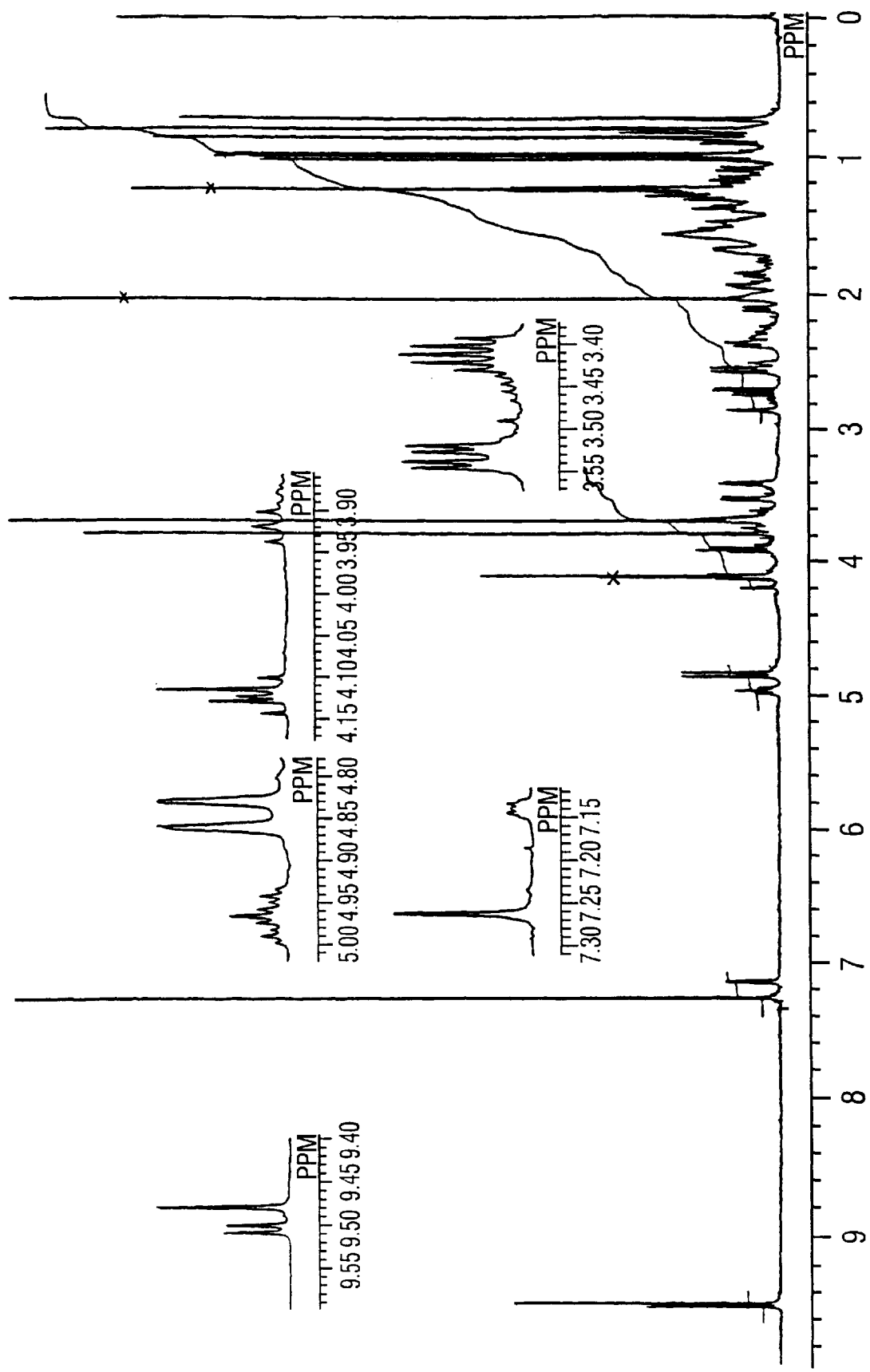
FIG. 22 shows $^1$H NMR (500 MHz; CDCl$_3$) spectrum and its partial magnifications of TG101-Me.
Figure 23:
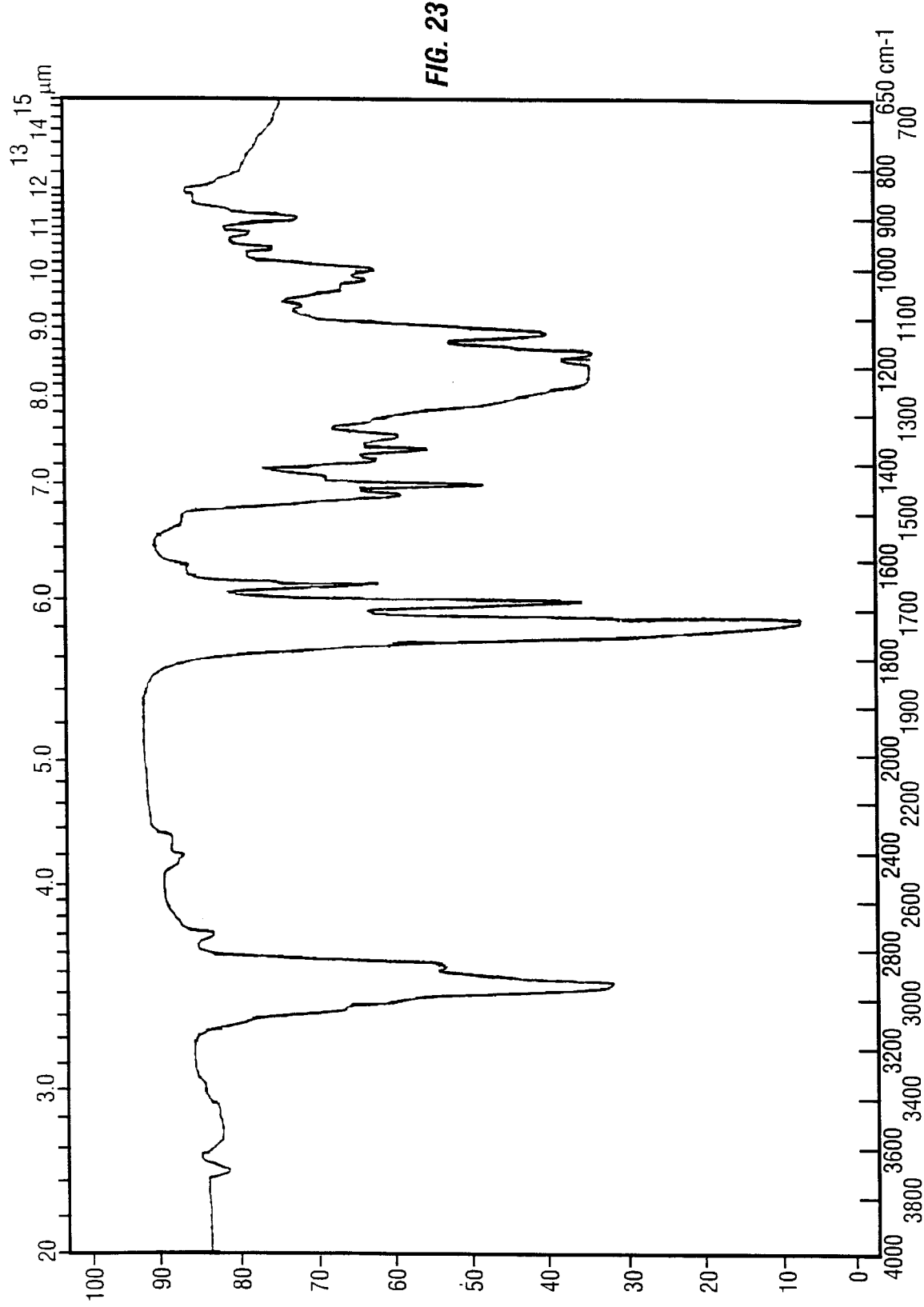
FIG. 23 shows an infrared absorption spectrum (KBr) of TG101-Me.

$^1$H NMR spectrum 500 MHz (CDCl$_3$) of TG101-Me is shown in FIG. 22, and its infrared absorption spectrum in FIG. 23.

On the other hand, as in the case of TG101, the methylation was carried out by adding 10% solution of trimethylsilyl diazomethane in n-hexane (0.6 ml) to a solution of TG103 (236 mg; 0.37 mmol) in ether/methanol (2 ml/2 ml). The reaction product was purified by silica gel column chromatography (silica gel, 5 g: 1.5 cm ID, eluent: n-hexane/ethyl acetate) to yield the methyl ester derivative of TG103 (TG103-Me, 220 mg) as white powder.

Figure 24:
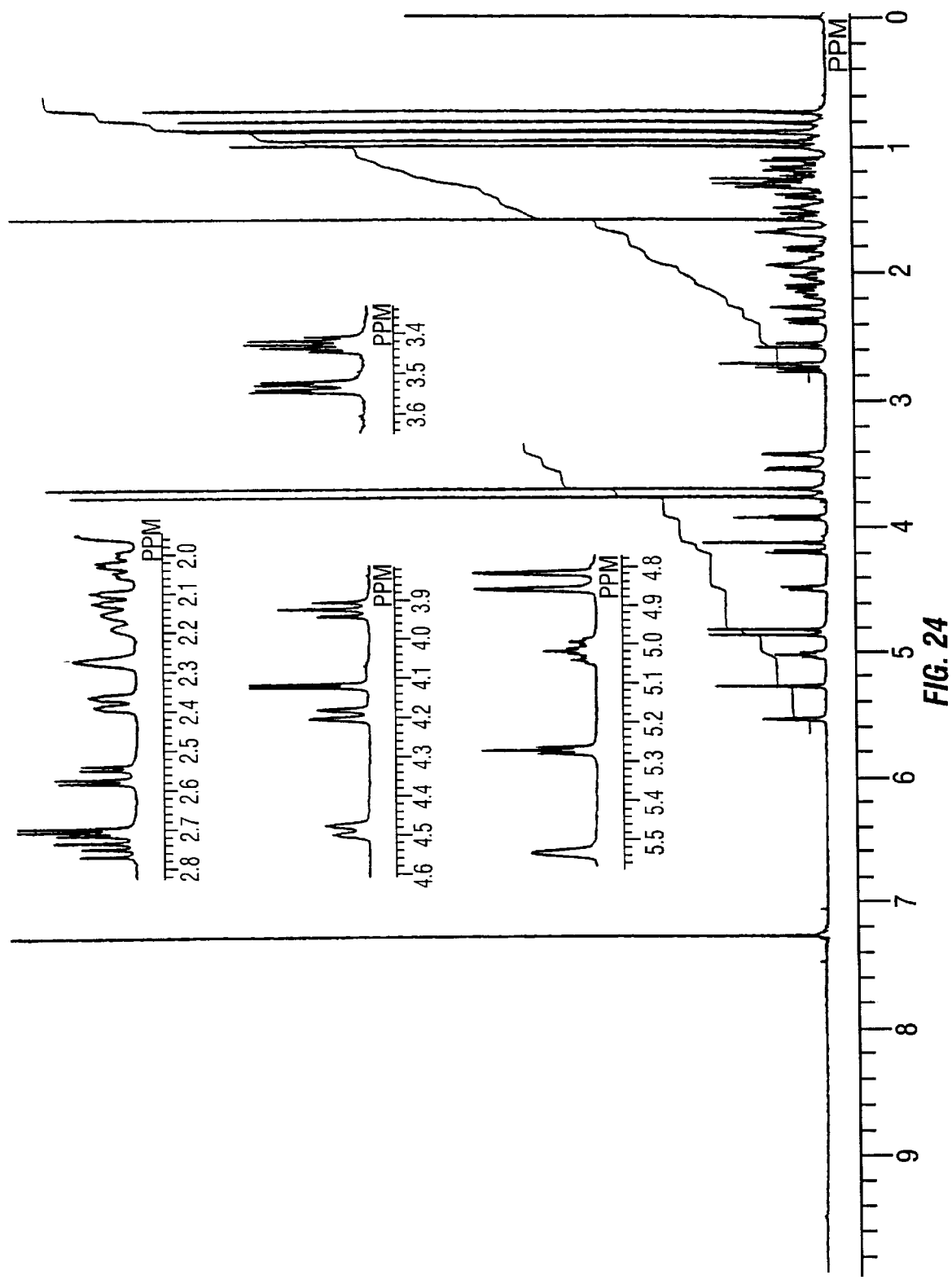
FIG. 24 shows $^1$H NMR (500 MHz; CDCl$_3$) spectrum and its partial magnifications of TG103-Me.
Figure 25:
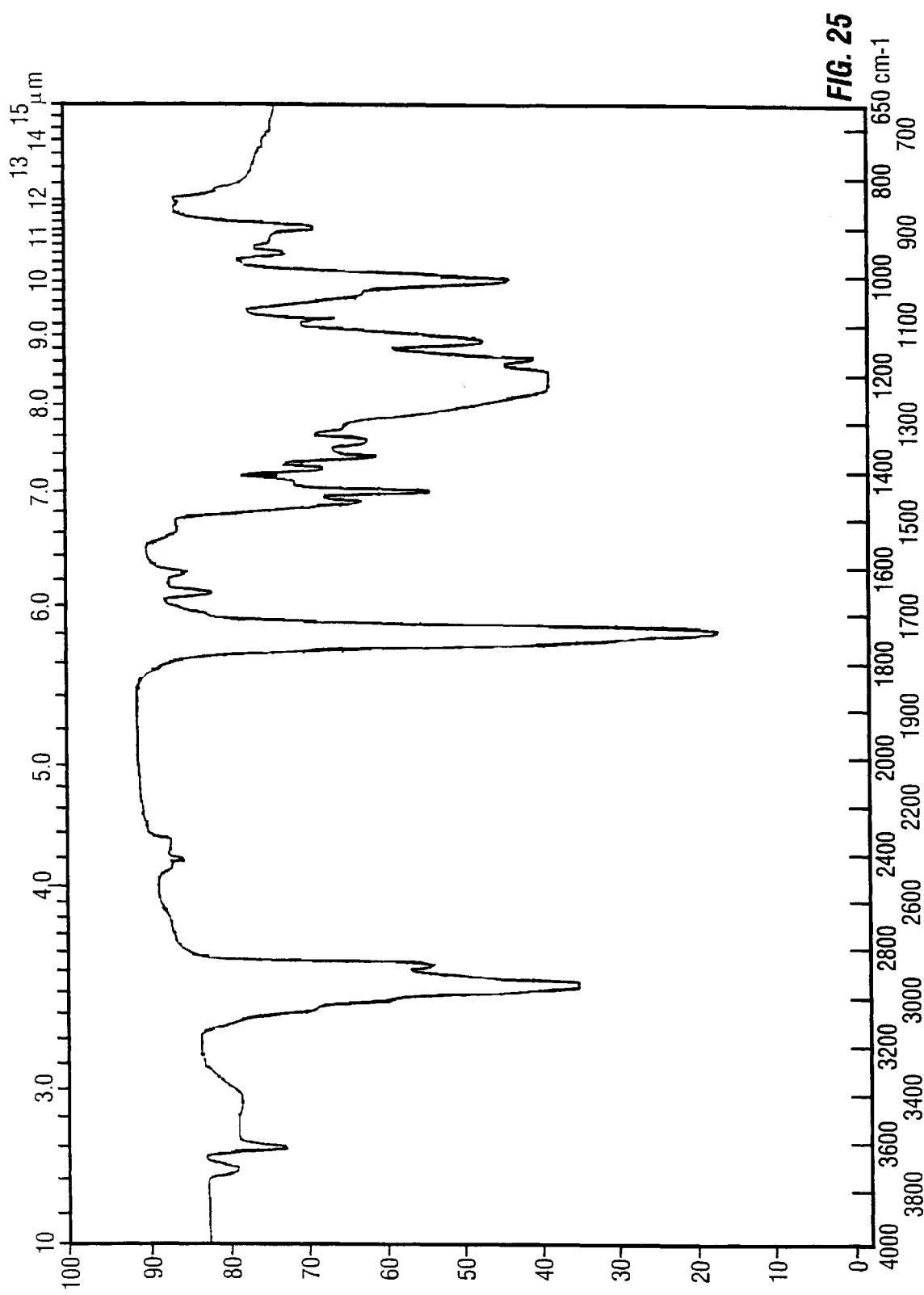
FIG. 25 shows an infrared absorption spectrum (KBr) of TG103-Me.

A 500 MHz $^1$H NMR spectrum (CDCl$_3$) of TG103-Me is shown in FIG. 24, and its infrared absorption spectrum (KBr) in FIG. 25.

Example 8

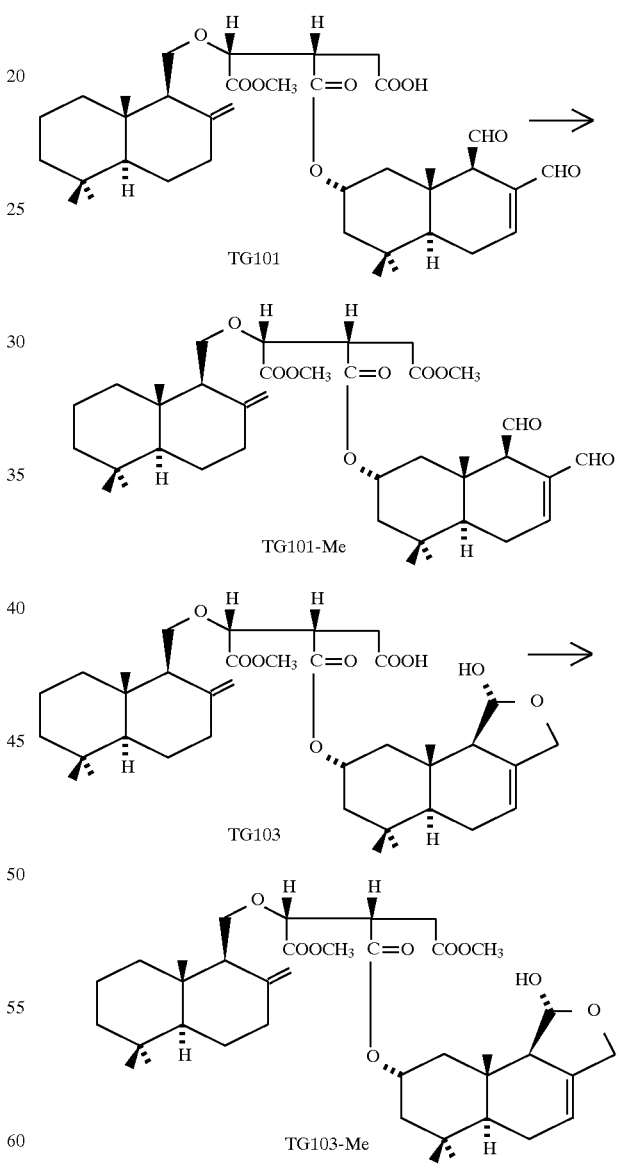

Pivaloyloxymethylation of TG101 and TG103

TG101 (96 mg: 0.15 mmol) was dissolved in dichloromethane (1 ml) and then added pivaloyloxymethyl chloride (43 µl: 0.3 mmol) and diisopropylethylamine (53 µl: 0.3 mmol) while stirring ice, and the reaction mixture was stirred for 48 h at room temperature. After the addition of water (10 ml), the reaction mixture was extracted with ethyl acetate twice. Combined extracts were successively washed with 1N hydrochloric acid, saturated sodium bicarbonate solution and saturated sodium chloride solution, and dried over magnesium sulfate. After the solvent was distilled off in vacuo, the residue was purified by silica gel column chromatography (silica gel, 6 g: 1.0 cm ID, eluent: chloroform/ethyl acetate) to obtain the pivaloyloxymethyl ester derivative of TG101 (TG101-POM, 40 mg) as white powder together with the recovery of unreacted starting material (17 mg).

Figure 26:
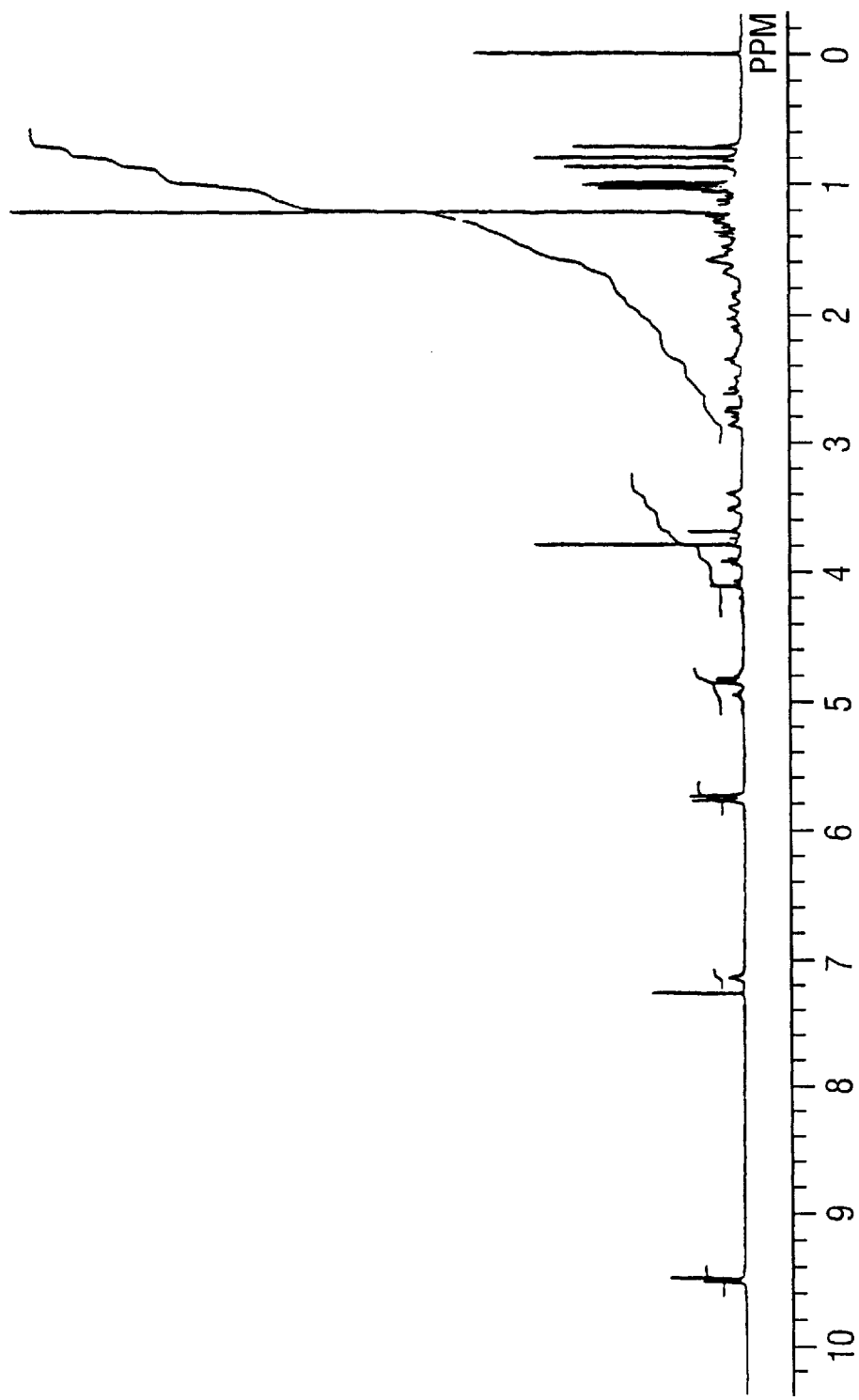
FIG. 26 shows $^1$H NMR (500 MHz; CDCl$_3$) spectrum of TG101-POM.
Figure 27:
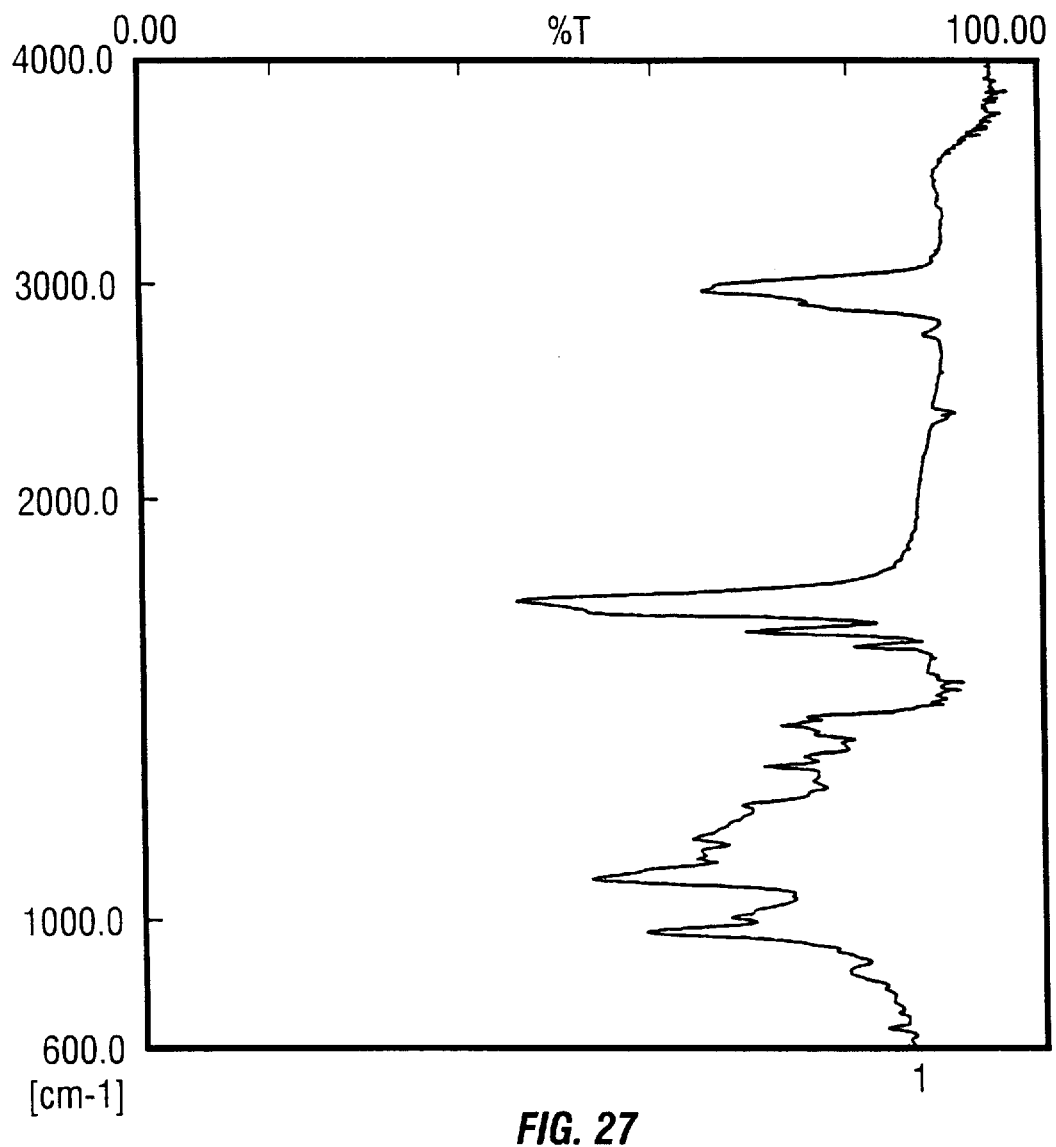
FIG. 27 shows an infrared absorption spectrum (KBr) of TG101-POM.

A 500 MHz $^1$H NMR spectrum (CDCl$_3$) of TG101-POM is shown in FIG. 26, and its infrared absorption spectrum (KBr) in FIG. 27.

On the other hand, as in the case of TG101, pivaloyloxymethyl chloride (70 μl: 0.48mmol) and diisopropylamine (84 μl: 0.48 mmol) were added to a solution of TG103 (128 mg: 0.2 mmol) in dichloromethane (1 ml). After the reaction was over, the reaction mixture was treated in the same way as in the case of TG101, and the product was purified by silica gel column chromatography (silica gel, 5 g; 1.0 cm ID; eluent, chloroform/ethyl acetate) to obtain the pivaloyloxymethylated derivative of TG103 (TG103-POM, 48 mg) as white powder with the recovery of unreacted starting material (19 mg).

Figure 28:
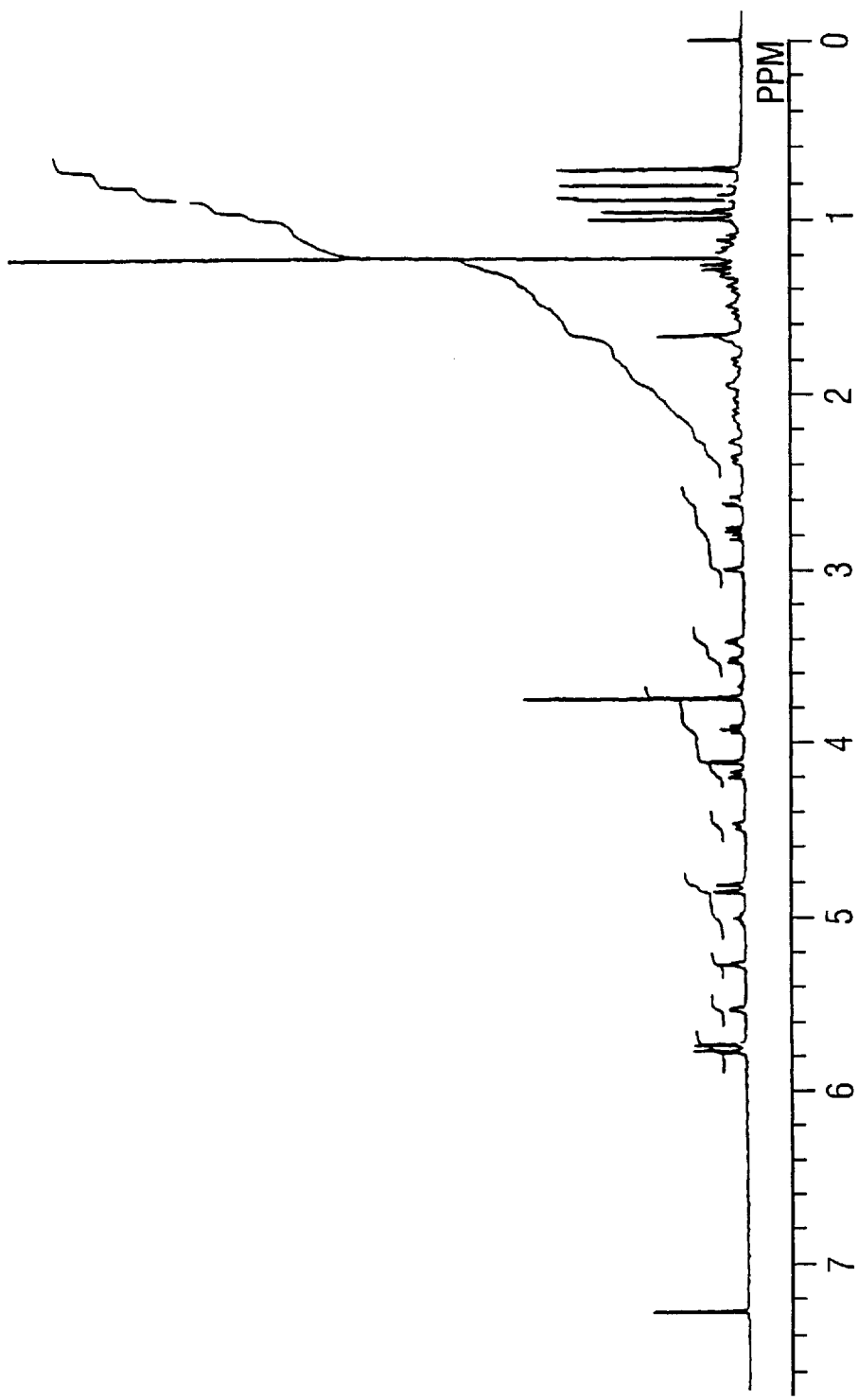
FIG. 28 shows $^1$H NMR (500 MHz; CDCl$_3$) spectrum of TG103-POM.
Figure 29:
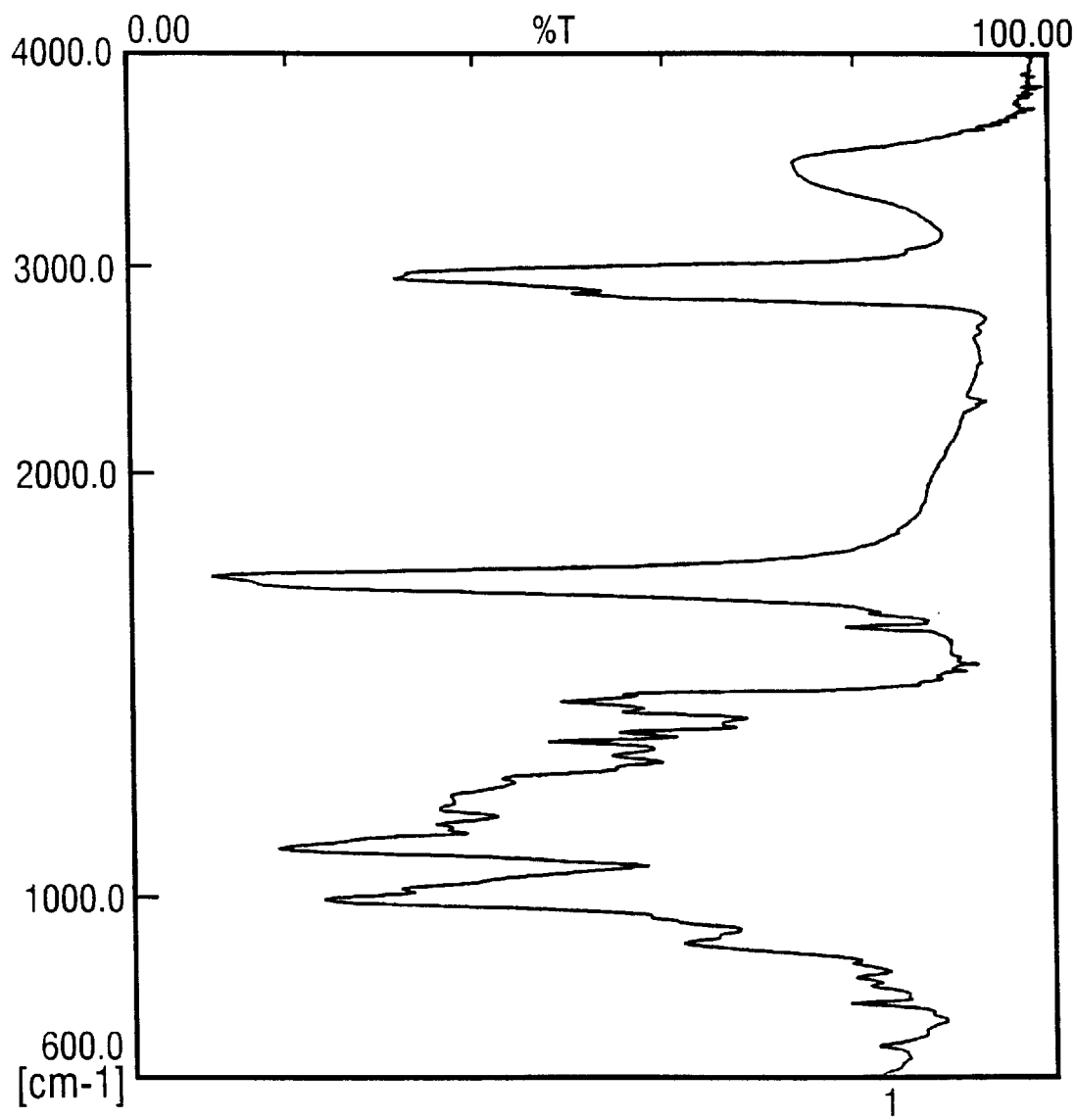
FIG. 29 shows an infrared absorption spectrum (KBr) of TG103-POM.

A 500 MHz $^1$H NMR spectrum (CDCl$_3$) of TG103-POM is shown in FIG. 28, and its infrared absorption spectrum (KBr) in FIG. 29.

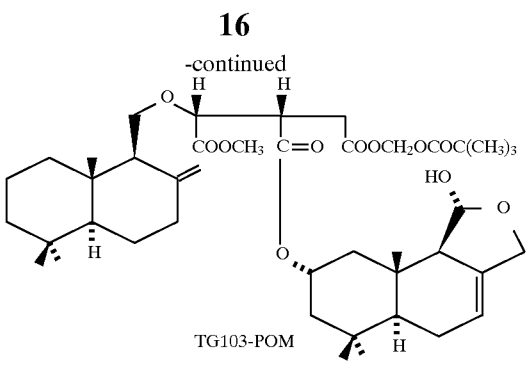

TG103-POM

Example 9

Synthesis of TG105

To a solution of TG101 (13 mg: 0.02 mmol) in methanol (1 ml) was added cerium (III) chloride heptahydrate (7.5 mg: 0.02 ml), and the reaction solution was stirred at room temperature for 20 min. After the end of the reaction was confirmed, the solvent was distilled off, and the residue was purified by silica gel column chromatography (eluent: chloroform/methanol) to obtain TG105 (13 mg) as white powder.

Figure 30:
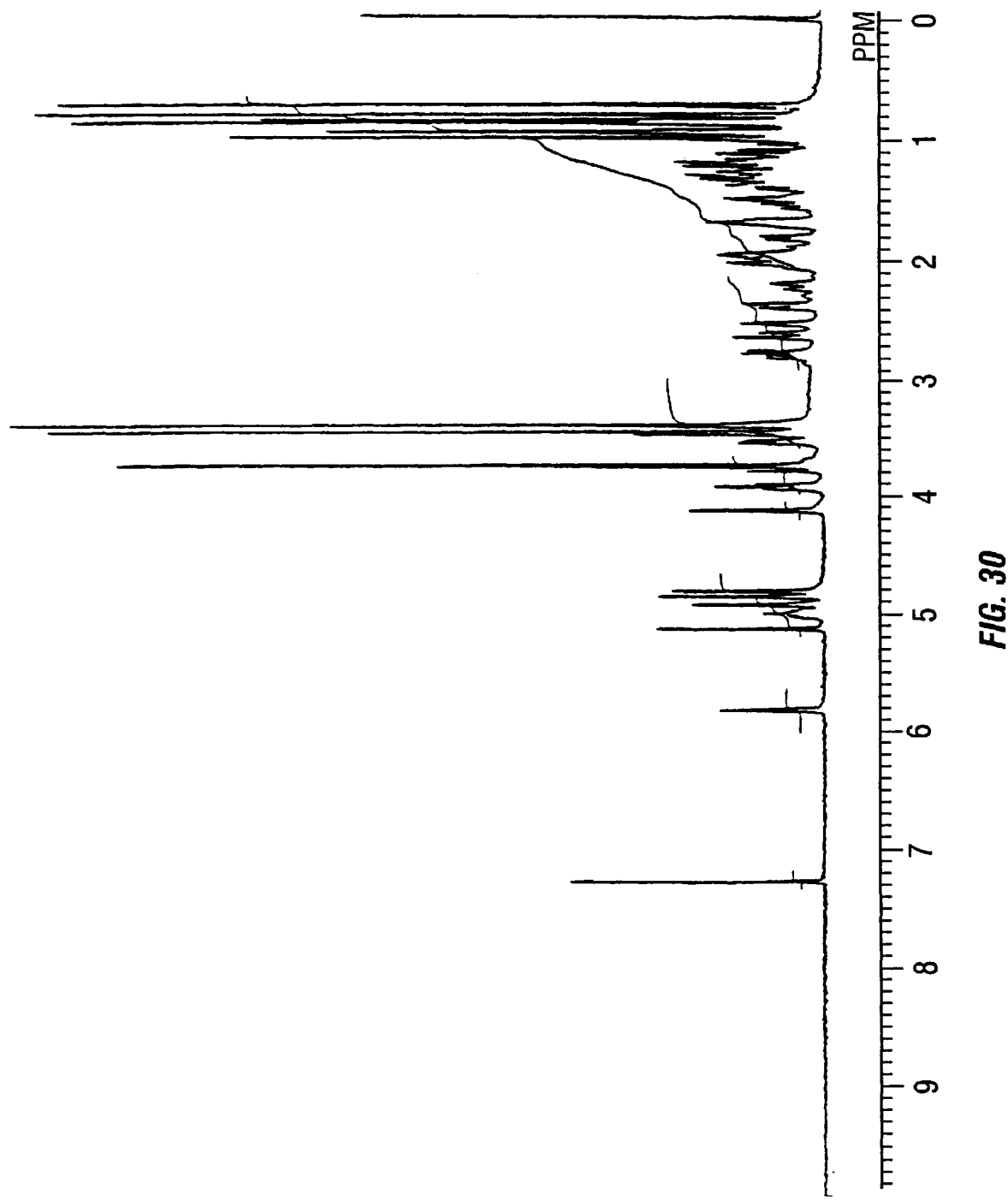
FIG. 30 shows $^1$H NMR (500 MHz; CDCl$_3$) spectrum of TG105.
Figure 31:
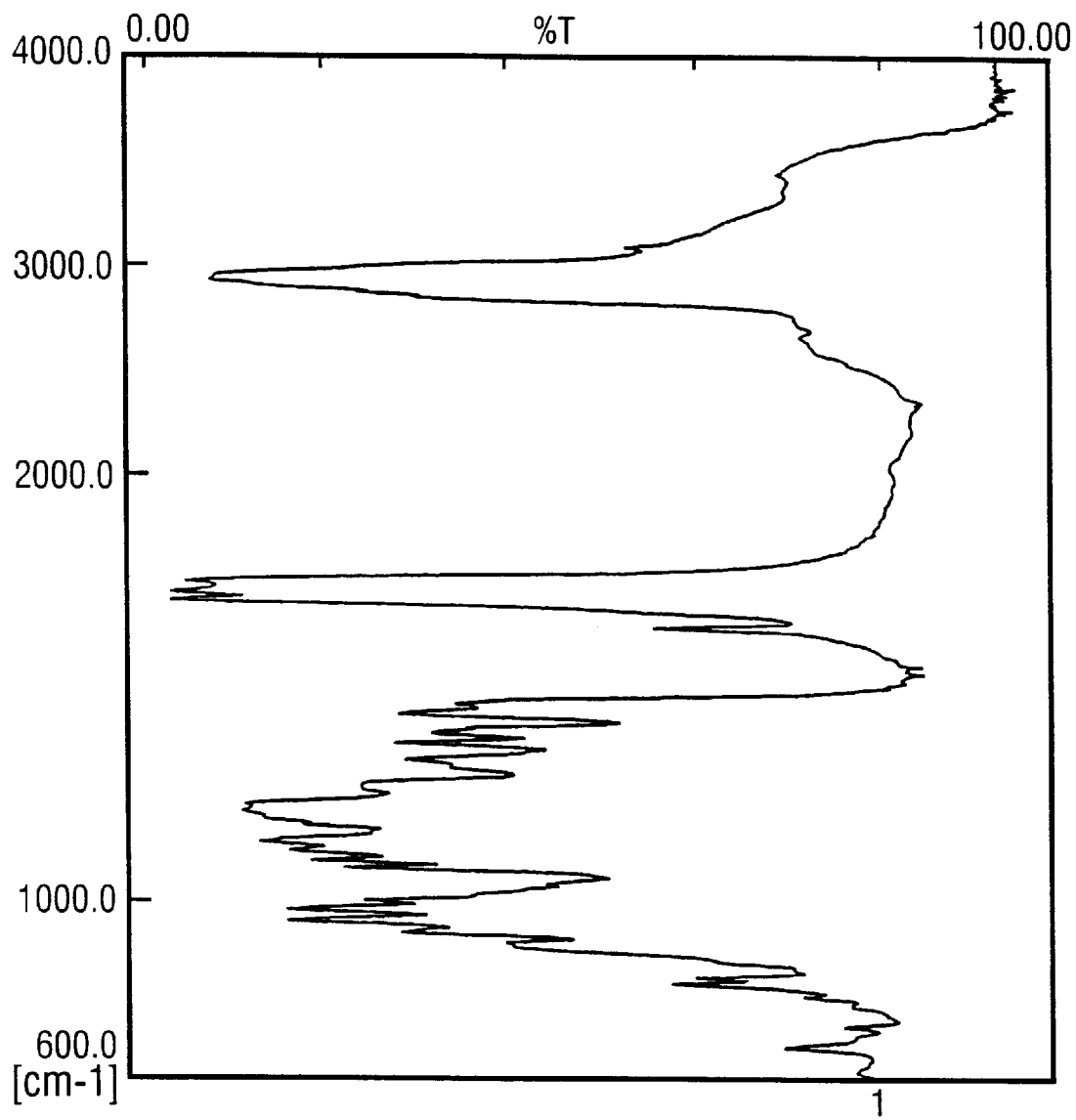
FIG. 31 shows an infrared absorption spectrum (KBr) of TG105.

A 500 MHz $^1$H NMR spectrum (CDCl$_3$) of TG105 is shown in FIG. 30, and its infrared absorption spectrum (KBr) in FIG. 31.

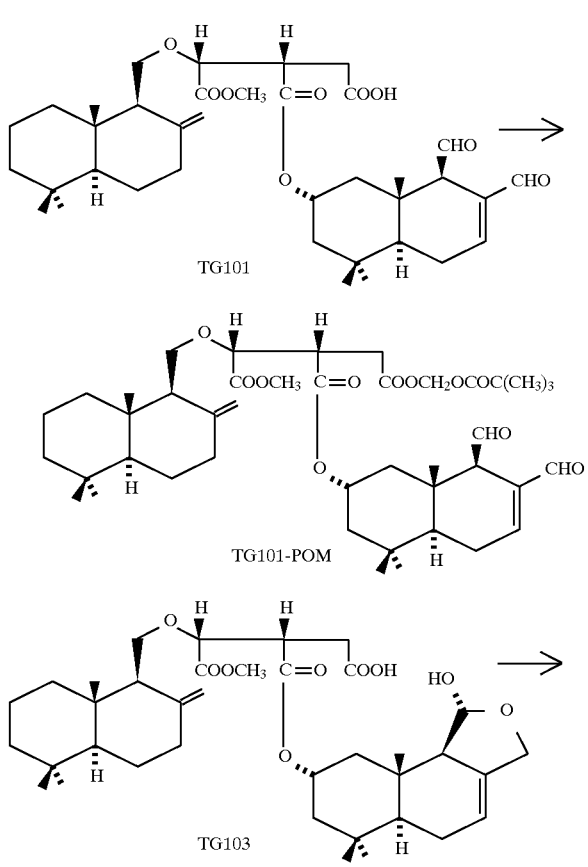

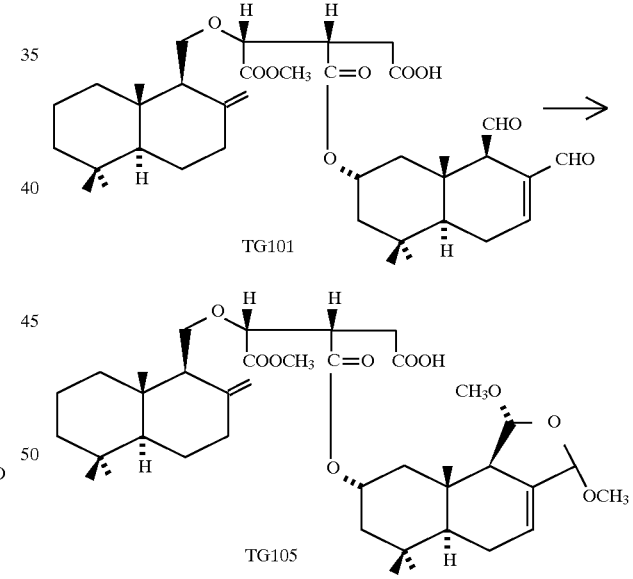

INDUSTRIAL APPLICABILITY

Novel sesquiterpene compounds of the present invention exhibit anti-fungal actions against eumycetes such as *Candida albicans,* and are useful as effective ingredients in anti-fungal drugs.

We claim:
1. A sesquiterpene compound represented by the following structural formula I:

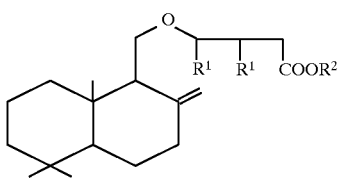 (I)

wherein one of the two $R^1$ groups present in said formula is a —$COOR^3$ group, and the other one is any one of the groups represented by the following formulas,

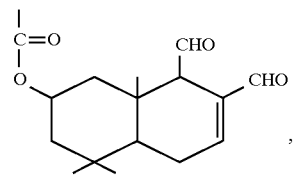

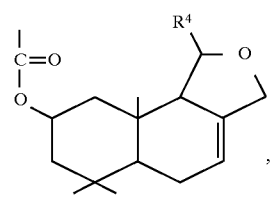

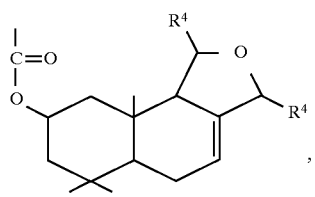

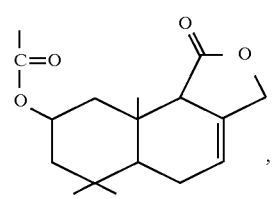

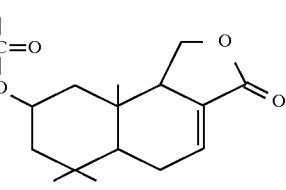

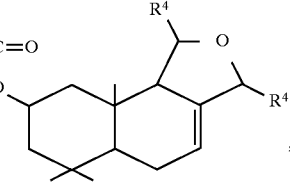

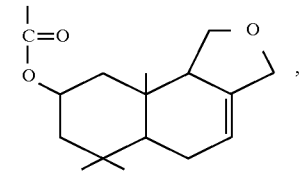

-continued

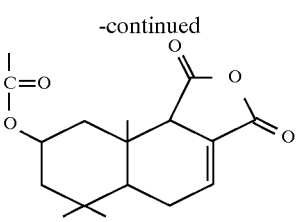

wherein each $R^2$ and $R^3$ group is independently a hydrogen atom, an alkyl group or an acyloxyalkyl group, and $R^4$ is a hydroxyl group or an alkoxy group.

2. The sesquiterpene compound according to claim 1, wherein $R^2$ and $R^3$ are independently methyl groups, respectively.

3. The sesquiterpene compound according to claim 1, wherein one or both of $R^2$ or $R^3$ is a t-butyl carbonyloxymethyl group.

4. The sesquiterpene compound according to claim 1, wherein $R^4$ is a hydroxyl group or methoxy group.

5. An anti-microbial composition containing a sesquiterpene compound and a carrier, the sesquiterpene compound being represented by the following structural formula II:

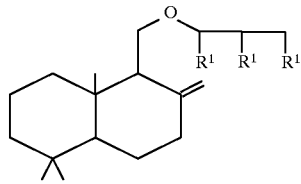 (II)

wherein $R^1$ is a —$COOR^2$ group in which $R^2$ is a hydrogen atom, an alkyl group or an acyloxyalkyl group, or any one of the groups represented by the following structural formulas:

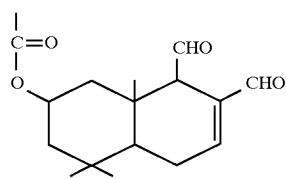

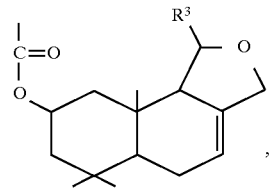

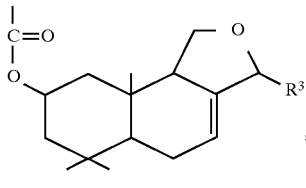

-continued

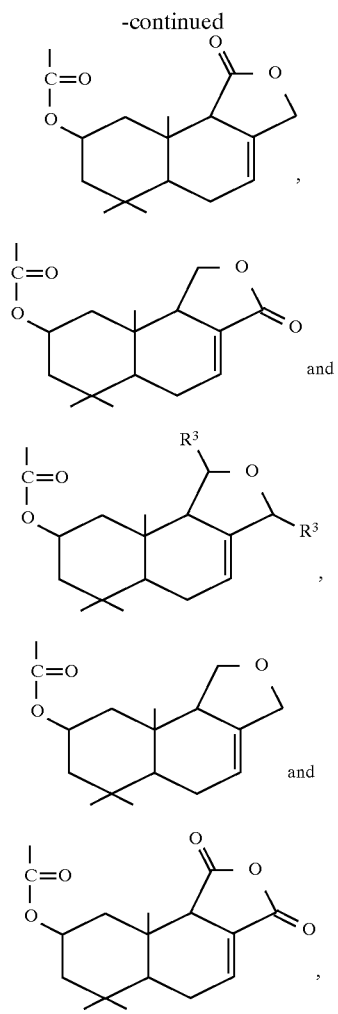

wherein R³ is a hydroxyl group or an alkoxy group.

6. An anti-microbial composition containing a sesquiterpene compound and a carrier, the sesquiterpene compound being represented by the following structural formula III:

(III)

wherein one of the two R¹ groups present in said formula is a —COOR³ group, and the second one is a —COOH group or any one of the groups represented by the following structural formulas,

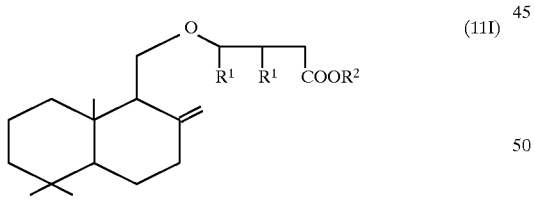

-continued

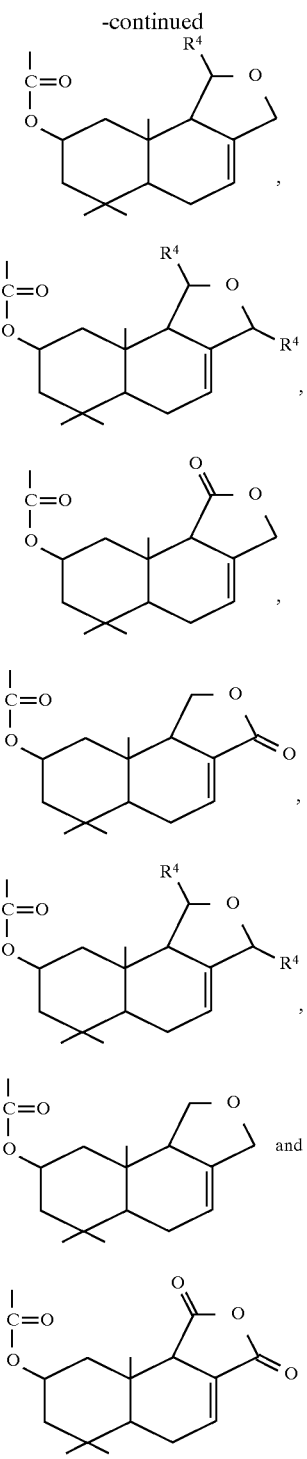

wherein R² and R³ are independently a hydrogen atom, an alkyl or an acyloxyalkyl group, respectively, or both are hydrogen atoms when the second R¹ is a —COOH group, and R⁴ is a hydroxyl group or an alkoxy group.

* * * * *